United States Patent
Ciceri et al.

(10) Patent No.: US 10,324,092 B2
(45) Date of Patent: Jun. 18, 2019

(54) DETECTABLE NUCLEIC ACID TAG

(71) Applicant: DiscoveRx Corporation, Fremont, CA (US)

(72) Inventors: Pietro Ciceri, San Diego, CA (US); Jeremy Hunt, San Diego, CA (US); Jean-Michel A. Lelias, Dana Point, CA (US); Mike Morrison, San Diego, CA (US); Daniel K. Treiber, San Diego, CA (US); Lisa Wodicka, San Diego, CA (US)

(73) Assignee: Eurofins DiscoverX Corporation, Fremont, CA (US)

( * ) Notice: Subject to any disclaimer, the term of this patent is extended or adjusted under 35 U.S.C. 154(b) by 697 days.

(21) Appl. No.: 14/811,335

(22) Filed: Jul. 28, 2015

(65) Prior Publication Data
US 2015/0377886 A1 Dec. 31, 2015

Related U.S. Application Data

(62) Division of application No. 11/824,325, filed on Jun. 29, 2007, now Pat. No. 9,110,054.

(60) Provisional application No. 60/806,422, filed on Jun. 30, 2006.

(51) Int. Cl.
| | |
|---|---|
| C12Q 1/68 | (2018.01) |
| G01N 33/532 | (2006.01) |
| G01N 33/573 | (2006.01) |
| G01N 33/58 | (2006.01) |
| C12Q 1/6806 | (2018.01) |

(52) U.S. Cl.
CPC ............ *G01N 33/573* (2013.01); *C12Q 1/68* (2013.01); *C12Q 1/6806* (2013.01); *G01N 33/532* (2013.01); *G01N 33/585* (2013.01); *G01N 2458/00* (2013.01)

(58) Field of Classification Search
None
See application file for complete search history.

(56) References Cited

U.S. PATENT DOCUMENTS

| | | | |
|---|---|---|---|
| 6,258,558 B1 * | 7/2001 | Szostak | C07K 14/82 435/69.1 |
| 7,183,395 B2 * | 2/2007 | Mauro | C12N 15/1048 435/320.1 |
| 2003/0027214 A1 * | 2/2003 | Kamb | C07K 1/047 506/4 |

FOREIGN PATENT DOCUMENTS

| | | |
|---|---|---|
| EP | 1138781 A2 | 10/2001 |
| WO | 99/27092 A1 | 6/1999 |
| WO | 2002/050259 A2 | 6/2002 |
| WO | 2003/083435 A2 | 10/2003 |
| WO | 2003/102221 A1 | 12/2003 |

(Continued)

OTHER PUBLICATIONS

Uetz et al. (Nature, 2000, vol. 403, 10: 623-627).*

(Continued)

*Primary Examiner* — Stephanie K Mummert
(74) *Attorney, Agent, or Firm* — Brian E. Davy; Bozicevic, Field & Francis LLP

(57) ABSTRACT

Provided herein are nucleic acid tags that are linked to, or capable of linking to, a protein of interest. In particular, the nucleic acid tags are oligonucleotides comprising a reporter function and a protein tagging function. Also provided herein, are nucleic acid tag compositions, kits and methods of use thereof.

23 Claims, 6 Drawing Sheets

Specification includes a Sequence Listing.

(56) References Cited

FOREIGN PATENT DOCUMENTS

WO    2004/035732    4/2004

OTHER PUBLICATIONS

Meyers et al. (Molecular Cellular Biology, 1993, 13(10):6336-6345) (Year: 1993).*

Seong et al. (Analytical Biochemistry, 2002, vol. 309, p. 241-247) (Year: 2002).*

Akiyama, et al., "The gem-motif: A novel DNA-binding motif conserved in *Drosophila* and mammals," PNAS (1996) 93:14912-14916.

Basu, et al., "The Intracisternal A-Particle Proximal Enhancer-Binding Protein Activates Transcription and Is Identical to the RNA- and DNA-Binding Protein p54nrb/NonO," Molecular and Cellular Biology (1997) 17(2):677-686.

Durfee, et al., "The retinoblastoma protein associates with the protein phosphatase type 1 catalytic subunit," Genes Dev. (1993) 7:555-569.

Escalante, et al., "Structure of IRF-1 with bound DNA reveals determinants of interferon regulation", Nature (1998) 391:103-106.

Kuprash, et al., "Homodimer of p50 (NFκB1) does not introduce a substantial directed bend into DNA according to three different experimental assays", Nucleic Acids Research (1995) 23(3):427-433.

Meyers, et al., "Identificaton of AML-1 and the (8;21) Translocation Protein (AML-1/ETO) as Sequence-Specific DNA-Binding Proteins: the runt Homology Domain Is Required for DNA Binding and Protein-Protein Interactons," Molecular and Cellular Biology (1993) 13(10):6336-6345.

Nehyba, et al., "Differences in κb DNA-binding properties of v-Rel and c-Rel are the result of oncogenic mutations in three distinct functional regions of the Rel protein", Oncogene (1997) 14:2881-2897.

Roberts, Richard W., et al., "RNA-peptide fusions for the in vitro selection of peptides and proteins," PNAS (1997) 94:12297-12302.

Roberts, Stefan G.E., et al., "The mouse proline-rich protein MP6 promoter binds isoprenaline-inducible parotid nuclear proteins via a highly conserved NfkB/rel-like site," Nucleic Acids Research (1991) 19(19):5205-5211.

Sano, et al, "Immuno-PCR: Very Sensitive Antigen Detection by Means of Specific Antibody-DNA Conjugates," Science (1992) 258(5079):120-122.

Schweitzer, et al., "Immunoassays with rolling circle DNA amplification: A versatile platform for ultrasensitive antigen detection," PNAS (2002) 97(18):10113-10119.

Seong, et al., "Atomic force microscopy identification of transcription factor NFκB bound to streptavidin-pin-holding DNA probe," Analytical Biochemistry (2002) 309:241-247.

Traxler, et al., "Tyrosine kinases as targets in cancer therapy—successes and failures," Expert Opin. Ther. Targ (2003) 7(2):215-234.

Wiltshire, et al., "Detection of Multiple Allergen-specific IgES on Microarrays by Immunoassay with Rolling Circle Amplification," Clinical Chemistry (2000) 46:1900-1993.

International Search Report, Int'l Appl. No. PCT/US2007/015089, dated Jun. 23, 2008.

Written Opinion, Int'l Appl. No. PCT/US2007/015089, dated Jun. 23, 2008.

Office Action, PRC Application No. 200780032387.7, dated Jul. 6, 2011.

* cited by examiner

```
                         SEQUENCE LISTING

<160> NUMBER OF SEQ ID NOS: 21

<210> SEQ ID NO 1
<211> LENGTH: 98
<212> TYPE: DNA
<213> ORGANISM: Artificial Sequence
<220> FEATURE:
<223> OTHER INFORMATION: Nucleic acid tag for NF-kB

<400> SEQUENCE: 1
ttgtgaattg ctgaccgtag atgtcaactt tgaccatcag acaacgtttc tccattccaa    60
ttatgcgaga atcctaggga attcccctag atcgcatg                            98

<210> SEQ ID NO 2
<211> LENGTH: 90
<212> TYPE: DNA
<213> ORGANISM: Artificial Sequence
<220> FEATURE:
<223> OTHER INFORMATION: Nucleic acid tag for NF-kB

<400> SEQUENCE: 2
cggcgtaaaa acgaatacca tgtctctcat cgctcgactc attctttcca aaatttcgcg    60
gaaccagggg gaattcccct agatcgcatg                                     90

<210> SEQ ID NO 3
<211> LENGTH: 94
<212> TYPE: DNA
<213> ORGANISM: Artificial Sequence
<220> FEATURE:
<223> OTHER INFORMATION: Nucleic acid tag for NF-kB

<400> SEQUENCE: 3
aaacaatgag acaccaggga ttagatatca gtacaatgtg cttccacaaa ggatcaccag    60
caatattcca aagggaattc ccctagatcg catg                                94
```

<210> SEQ ID NO 4
<211> LENGTH: 107
<212> TYPE: DNA
<213> ORGANISM: Artificial Sequence
<220> FEATURE:
<223> OTHER INFORMATION: Nucleic acid tag for GAL4 binding

<400> SEQUENCE: 4

```
catgcgacag cggagttacg tccagaagga caacatcttt gacatcgcct cttgaattgc      60
tgcaccaagg gctactgccg gagtactgtc ctccgctaga tcgcatg                    107
```

<210> SEQ ID NO 5
<211> LENGTH: 322
<212> TYPE: PRT
<213> ORGANISM: Artificial Sequence
<220> FEATURE:
<223> OTHER INFORMATION: NF-kB DNA binding domain

<400> SEQUENCE: 5

```
Met Ala Gly Pro Tyr Leu Gln Ile Leu Glu Gln Pro Lys Gln Arg Gly
  1               5                  10                  15

Phe Arg Phe Arg Tyr Val Cys Glu Gly Pro Ser His Gly Gly Leu Pro
                 20                  25                  30

Gly Ala Ser Ser Glu Lys Asn Lys Lys Ser Tyr Pro Gln Val Lys Ile
             35                  40                  45

Cys Asn Tyr Val Gly Pro Ala Lys Val Ile Val Gln Leu Val Thr Asn
 50                  55                  60

Gly Lys Asn Ile His Leu His Ala His Ser Leu Val Gly Lys His Cys
 65                  70                  75                  80

Glu Asp Gly Ile Cys Thr Val Thr Ala Gly Pro Lys Asp Met Val Val
                 85                  90                  95

Gly Phe Ala Asn Leu Gly Ile Leu His Val Thr Lys Lys Lys Val Phe
                100                 105                 110

Glu Thr Leu Glu Ala Arg Met Thr Glu Ala Cys Ile Arg Gly Tyr Asn
            115                 120                 125

Pro Gly Leu Leu Val His Pro Asp Leu Ala Tyr Leu Gln Ala Glu Gly
        130                 135                 140

Gly Gly Asp Arg Gln Leu Gly Asp Arg Glu Lys Glu Leu Ile Arg Gln
145                 150                 155                 160

Ala Ala Leu Gln Gln Thr Lys Glu Met Asp Leu Ser Val Val Arg Leu
                165                 170                 175

Met Phe Thr Ala Phe Leu Pro Asp Ser Thr Gly Ser Phe Thr Arg Arg
            180                 185                 190

Leu Glu Pro Val Val Ser Asp Ala Ile Tyr Asp Ser Lys Ala Pro Asn
        195                 200                 205

Ala Ser Asn Leu Lys Ile Val Arg Met Asp Arg Thr Ala Gly Cys Val
    210                 215                 220

Thr Gly Gly Glu Glu Ile Tyr Leu Leu Cys Asp Lys Val Gln Lys Asp
225                 230                 235                 240

Asp Ile Gln Ile Arg Phe Tyr Glu Glu Glu Asn Gly Gly Val Trp
                245                 250                 255

Glu Gly Phe Gly Asp Phe Ser Pro Thr Asp Val His Arg Gln Phe Ala
            260                 265                 270

Ile Val Phe Lys Thr Pro Lys Tyr Lys Asp Ile Asn Ile Thr Lys Pro
        275                 280                 285

Ala Ser Val Phe Val Gln Leu Arg Arg Lys Ser Asp Leu Glu Thr Ser
    290                 295                 300
```

```
Glu Pro Lys Pro Phe Leu Tyr Tyr Pro Glu Ile Lys Asp Lys Glu Glu
305                 310                 315                 320

Val Asp

<210> SEQ ID NO 6
<211> LENGTH: 147
<212> TYPE: PRT
<213> ORGANISM: Artificial Sequence
<220> FEATURE:
<223> OTHER INFORMATION: GAL4 DA binding domain

<400> SEQUENCE: 6

Met Lys Leu Leu Ser Ser Ile Glu Gln Ala Cys Asp Ile Cys Arg Leu
1               5                   10                  15

Lys Lys Leu Lys Cys Ser Lys Glu Lys Pro Lys Cys Ala Lys Cys Leu
            20                  25                  30

Lys Asn Asn Trp Glu Cys Arg Tyr Ser Pro Lys Thr Lys Arg Ser Pro
        35                  40                  45

Leu Thr Arg Ala His Leu Thr Glu Val Glu Ser Arg Leu Glu Arg Leu
    50                  55                  60

Glu Gln Leu Phe Leu Leu Ile Phe Pro Arg Glu Asp Leu Asp Met Ile
65                  70                  75                  80

Leu Lys Met Asp Ser Leu Gln Asp Ile Lys Ala Leu Leu Thr Gly Leu
                85                  90                  95

Phe Val Gln Asp Asn Val Asn Lys Asp Ala Val Thr Asp Arg Leu Ala
            100                 105                 110

Ser Val Glu Thr Asp Met Pro Leu Thr Leu Arg Gln His Arg Ile Ser
        115                 120                 125

Ala Thr Ser Ser Ser Glu Glu Ser Ser Asn Lys Gly Gln Arg Gln Leu
    130                 135                 140

Thr Val Ser
145

<210> SEQ ID NO 7
<211> LENGTH: 10
<212> TYPE: DNA
<213> ORGANISM: Artificial Sequence
<220> FEATURE:
<223> OTHER INFORMATION: NF-kB recognition sequence

<400> SEQUENCE: 7
gggaattccc                                                            10

<210> SEQ ID NO 8
<211> LENGTH: 11
<212> TYPE: DNA
<213> ORGANISM: Artificial Sequence
<220> FEATURE:
<223> OTHER INFORMATION: NF-kB recognition sequence

<400> SEQUENCE: 8
gggaaattcc c                                                          11

<210> SEQ ID NO 9
<211> LENGTH: 10
<212> TYPE: DNA
<213> ORGANISM: Artificial Sequence
<220> FEATURE:
<223> OTHER INFORMATION: NF-kB recognition sequence

<400> SEQUENCE: 9
```

```
gggactttcc                                                              10

<210> SEQ ID NO 10
<211> LENGTH: 10
<212> TYPE: DNA
<213> ORGANISM: Artificial Sequence
<220> FEATURE:
<221> NAME/KEY: VARIANT
<222> LOCATION: 4
<223> OTHER INFORMATION: R = Purine
<220> FEATURE:
<221> NAME/KEY: VARIANT
<222> LOCATION: 5, 6
<223> OTHER INFORMATION: N = Any nucleic acid
<220> FEATURE:
<221> NAME/KEY: VARIANT
<222> LOCATION: 7, 8
<223> OTHER INFORMATION: Y = Pyrimidine
<220> FEATURE:
<223> OTHER INFORMATION: NF-kB consensus sequence

<400> SEQUENCE: 10 gggrnnyycc                                                              10

<210> SEQ ID NO 11
<211> LENGTH: 17
<212> TYPE: DNA
<213> ORGANISM: Artificial Sequence
<220> FEATURE:
<223> OTHER INFORMATION: GAL4 recognition sequence

<400> SEQUENCE: 11
cggagtactg tcctccg                                                      17

<210> SEQ ID NO 12
<211> LENGTH: 17
<212> TYPE: DNA
<213> ORGANISM: Artificial Sequence
<220> FEATURE:
<221> NAME/KEY: VARIANT
<222> LOCATION: 4, 5, 6, 7, 8, 9, 10, 11, 12, 13, 14
<223> OTHER INFORMATION: N = Any nucleic acid
<220> FEATURE:
<223> OTHER INFORMATION: GAL4 consensus sequence

<400> SEQUENCE: 12
cggnnnnnnn nnnnccg                                                      17

<210> SEQ ID NO 13
<211> LENGTH: 10
<212> TYPE: DNA
<213> ORGANISM: Artificial Sequence
<220> FEATURE:
<221> NAME/KEY: VARIANT
<222> LOCATION: 1
<223> OTHER INFORMATION: H = A, C, or T
<220> FEATURE:
<221> NAME/KEY: VARIANT
<222> LOCATION: 5
<223> OTHER INFORMATION: R = Purine
<220> FEATURE:
<221> NAME/KEY: VARIANT
<222> LOCATION: 6
<223> OTHER INFORMATION: N = Any nucleic acid
<220> FEATURE:
<221> NAME/KEY: VARIANT
<222> LOCATION: 7, 8
<223> OTHER INFORMATION: Y = Pyrimidine
<220> FEATURE:
<223> OTHER INFORMATION: RelA/c-Rel consensus sequence
```

<400> SEQUENCE: 13 hggarnyycc                                                               10

<210> SEQ ID NO 14
<211> LENGTH: 21
<212> TYPE: DNA
<213> ORGANISM: Artificial Sequence
<220> FEATURE:
<223> OTHER INFORMATION: Cro repressor recognition sequence

<400> SEQUENCE: 14
tctatcaccg cgggtgataa a                                                  21

<210> SEQ ID NO 15
<211> LENGTH: 22
<212> TYPE: DNA
<213> ORGANISM: Artificial Sequence
<220> FEATURE:
<223> OTHER INFORMATION: Lac repressor recognition sequence

<400> SEQUENCE: 15
ggaattgtga gcgctcacaa tt                                                 22

<210> SEQ ID NO 16
<211> LENGTH: 10
<212> TYPE: DNA
<213> ORGANISM: Artificial Sequence
<220> FEATURE:
<223> OTHER INFORMATION: GCN4 recognition sequence

<400> SEQUENCE: 16
agtgactcat                                                               10

<210> SEQ ID NO 17
<211> LENGTH: 22
<212> TYPE: DNA
<213> ORGANISM: Artificial Sequence
<220> FEATURE:
<223> OTHER INFORMATION: Opaque-2 recognition sequence

<400> SEQUENCE: 17
tgtcattcca cgtagatgaa aa                                                 22

<210> SEQ ID NO 18
<211> LENGTH: 10
<212> TYPE: DNA
<213> ORGANISM: Artificial Sequence
<220> FEATURE:
<223> OTHER INFORMATION: Opaque-2 recognition sequence

<400> SEQUENCE: 18
tccacgtaga                                                               10

<210> SEQ ID NO 19
<211> LENGTH: 16
<212> TYPE: DNA
<213> ORGANISM: Artificial Sequence
<220> FEATURE:
<223> OTHER INFORMATION: Lex-A recognition sequence

<400> SEQUENCE: 19
ctgtatatat atacag                                                        16

<210> SEQ ID NO 20
<211> LENGTH: 6

```
<212> TYPE: DNA
<213> ORGANISM: Artificial Sequence
<220> FEATURE:
<223> OTHER INFORMATION: TGA1a recognition sequence

<400> SEQUENCE: 20 gacgtc                                                                    6

<210> SEQ ID NO 21
<211> LENGTH: 10
<212> TYPE: DNA
<213> ORGANISM: Artificial Sequence
<220> FEATURE:
<223> OTHER INFORMATION: EGR-1 or Zif 268 recognition sequence

<400> SEQUENCE: 21
gcgtgggcgt                                                               10
```

DETECTABLE NUCLEIC ACID TAG

CROSS-REFERENCE TO RELATED APPLICATIONS

This application is a divisional application of U.S. patent application Ser. No. 11/824,325, filed Jun. 29, 2007, which claims priority from U.S. Provisional Patent Application No. 60/806,422, filed Jun. 30, 2006, both of which are hereby incorporated by reference in their entireties.

REFERENCE TO SEQUENCE LISTING, COMPUTER PROGRAM, OR COMPACT DISK

In accordance with "Legal Framework for EFS-Web," (6 Apr. 2011) Applicant submits herewith a sequence listing as an ASCII text file. The text file will serve as both the paper copy required by 37 CFR 1.821(c) and the computer readable form (CRF) required by 37 CFR 1.821(e). The date of creation of the file was Jul. 28, 2015, and the size of the ASCII text file in bytes is 8,863.

FIELD

The subject matter provided herein relates to nucleic acid tags that are linked to, or capable of linking to, a protein of interest. In particular, the present subject matter provided herein relates to oligonucleotides comprising a reporter function and a protein tagging function. Also provided herein, are nucleic acid tag compositions, kits and methods of use thereof.

BACKGROUND

Traditional techniques for quantifying and detecting the presence of proteins include gel electrophoresis, Western blotting, ELISA based immunoabsorbent assays and protein microarrays. Each of these methods are cumbersome and not amenable to high-throughput use. These traditional methods also suffer limitations in detection sensitivity and specificity. Provided herein is a nucleic acid tag and a new, highly sensitive and selective method of protein detection using the nucleic acid tags.

SUMMARY

Provided herein is a nucleic acid tag that is linked to or capable of linking to a protein, which allows the protein to be detected with a high degree of sensitivity. In one embodiment, the nucleic acid tag is an oligonucleotide having a reporter function and a protein tagging function. In one embodiment, the oligonucleotide (oligomer) is an oligonucleotide, which comprises a first nucleic acid sequence that is a PCR amplification sequence (an amplicon) recognizable by a PCR probe and a second nucleic acid sequence, which covalently links, non-covalently links, complexes or otherwise binds (e.g., binds to or is capable of binding to) a protein of interest. In certain embodiments, the amplicon is a randomly generated, non-naturally occurring PCR amplification sequence. In one embodiment, the first nucleic acid sequence and/or second nucleic acid sequence is not endogenous to a living organism. In other embodiments, first nucleic acid sequence and/or second nucleic acid sequence is endogenous to a living organism. In certain embodiments, the first nucleic acid sequence and the second nucleic acid sequence are heterologous. As used herein, if two nucleic acid sequences are "heterologous," it is meant that the first and second nucleic acid sequence are not normally found together. For example, in certain embodiments, the first and second nucleic acids do not encode the same protein and/or are not derived from the same organism. In some embodiments, the first sequence is a naturally occurring sequence and the second sequence is a naturally occurring sequence, wherein the first and second sequences differ. In specific embodiments, the first nucleic acid sequence is a nucleic acid sequence, such as a synthetic and/or randomly generated nucleic acid sequence, such as a non-naturally occurring sequence (e.g., one that is divergent from any naturally occurring sequence). In certain embodiments, the first nucleic acid sequence is a nucleic acid sequence, such as a synthetic and/or randomly generated nucleic acid sequence, that is not, for example, found in protein of interest, fusion protein, nucleic acid-interacting motif, and/or vectors used in a screening assay provided herein. In some embodiments, the first nucleic acid sequence is a nucleic acid sequence, such as a synthetic and/or randomly generated nucleic acid sequence, that is not present in the human kinome, such as when the nucleic acid tag is to be used in a kinase assay provided herein (or any other nucleotide sequence used in the given assay). These embodiment ensures, for example, that primers used for subsequence PCR amplification do not cross react or misprime to a second DNA sequence and/or to any other (e.g., naturally occurring) DNA sequence, such as those being used in a given assay. In certain embodiments, each PCR template is different from the others so that there is no chance of primers cross-reacting between templates, such as when used in the multiplex assays provided herein.

In another embodiment, the oligonucleotide comprises a first nucleic acid sequence comprising a PCR amplification sequence and a second nucleic acid sequence comprising a nucleic acid sequence which is a target sequence for and binds a nucleic acid interacting motif. In one example, the target sequence is a recognition sequence for either a naturally-occurring or synthetic DNA-binding protein. In specific embodiments, the first nucleic acid sequence comprising the PCR amplification sequence is separate and distinct from the second nucleic acid comprising the nucleic acid-interacting motif. In such embodiments, the nucleic acid tag is capable of binding or otherwise linking to a protein of interest having a DNA-binding component specifically recognizing the nucleic acid tag. The nucleic acid tag may then be detected and/or quantified using, e.g., quantitative PCR (qPCR). Nucleic acid tag detection by qPCR has the advantage of being not only a reliable quantitative detection method but also a highly sensitive and highly selective detection method. Because of the highly sensitive nature of the qPCR detection method, this method enables the detection of very small amounts of the target protein and reduces the need for scarce and expensive assay components, such as recombinant proteins. Because of the highly specific nature of the qPCR detection method, qPCR also enables the detection of specific DNA sequences in complex heterogeneous mixtures, and obviates the need for any sort of purification steps normally done to protein samples to either improve or enhance protein detection.

The nucleic acid tag provided herein may also be labeled, such as radiolabeled, fluorescently labeled or biotinylated. In certain embodiments, provided herein is a nucleic acid oligomer that binds a nucleic acid-interacting motif, wherein the nucleic acid oligomer comprises (a) a first radiolabeled, fluorescently labeled or biotinylated nucleic acid sequence, and (b) a second nucleic acid sequence that binds the nucleic acid-interacting motif. In other embodiments, provided herein is a nucleic acid oligomer comprising a nucleic acid sequence that binds a nucleic acid-interacting motif, wherein the oligomer is radiolabeled, fluorescently labeled or biotinylated. The labeled tags, such as radiolabeled or fluorescently labeled tags, may, for example, be used to detect the presence or locality of a protein of interest in cellular imaging or in visualization assays. The labeled tags, such as fluorescently labeled tags, may also, for example, be used in sorting assays to separate out one or more proteins of interest into individual samples. The labeled tags, such as biotinylated tags, also permit, for example, the detection of the protein of interest by immunological methods or the purification of the labeled protein of interest by affinity chromatography. In certain embodiments when the nucleic acid tag is labeled, the nucleic acid tag may or may not also comprise a PR amplification sequence.

Also provided herein is a protein of interest, which is linked or otherwise complexed to a nucleic acid tag or capable of linking or otherwise complexing to the nucleic acid tag, and which is therefore detectable when, for example, its function, activity or presence is being studied or monitored. In one example, the protein of interest is a chimeric protein fused to a nucleic acid interacting motif. In one example, the nucleic acid interacting motif is a DNA-binding domain. Such a protein of interest may be tagged by a nucleic acid having a target sequence that can be recognized by a DNA-binding domain. The chimeric protein may be an expressed nucleotide sequence generated by random mutation, an expressed nucleotide sequence containing systematically synthesized sequences, an expressed cDNA, or a combination of two or more of these possibilities. The protein of interest may be cloned and then expressed in an appropriate host cell, such as a bacterial, insect, mammalian or plant host cell. In certain embodiments, the host cell gives the protein the benefit of any post-translational modifications that may be important for its three dimensional structure and function (e.g., glycosylation or prenylation of the protein of interest in a human host cell).

Also provided herein is a method of detecting binding between a protein of interest and a second molecule, using a nucleic acid tag to label and detect the protein. In certain embodiments, the method comprises screening a library of test compounds for their ability to bind to a protein of interest, wherein the binding is identified by the detection of the nucleic acid tag. In other embodiments, the method comprises competition binding assays to screen for and determine the identity of one or more test compounds, which competitively bind to a protein of interest in the presence of an immobilized reference ligand (or "bait") that is known to bind to the protein of interest. Such a competitive binding assay allows the identification of alternative compounds which bind to the protein of interest in addition to (or preferentially to) the known reference ligand.

Also provided herein is a method comprising screening a test compound against a panel of proteins of interest for the ability of the test compound to bind to one or more proteins in the panel and/or to generate a binding specificity profile for that compound. Where the screening is performed against a panel of proteins, in some embodiments, the screening is done in a multiplexed format, such as by simultaneously testing the activity of a test compound against a pooled sample containing multiple proteins of interest, and/or at the detection step by using multiple nucleic acid tags that are each unique for a specific protein of interest.

Also provided herein is a kit comprising one or more of the following elements: a detectable nucleic acid tag, a protein capable of being "tagged" by the nucleic acid tag, an immobilized reference ligand that binds to the protein of interest, and a PCR primer pair capable of initiating amplification of the nucleic acid tag. Such a kit may be used to identify molecules that bind to the immobilized reference ligand and/or that compete with the immobilized ligand for binding to the protein of interest. Alternatively, the kit may be used as a diagnostic tool for detecting in a given specimen the presence of a molecule that binds to the immobilized reference ligand.

DETAILED DESCRIPTION

Figure 1:
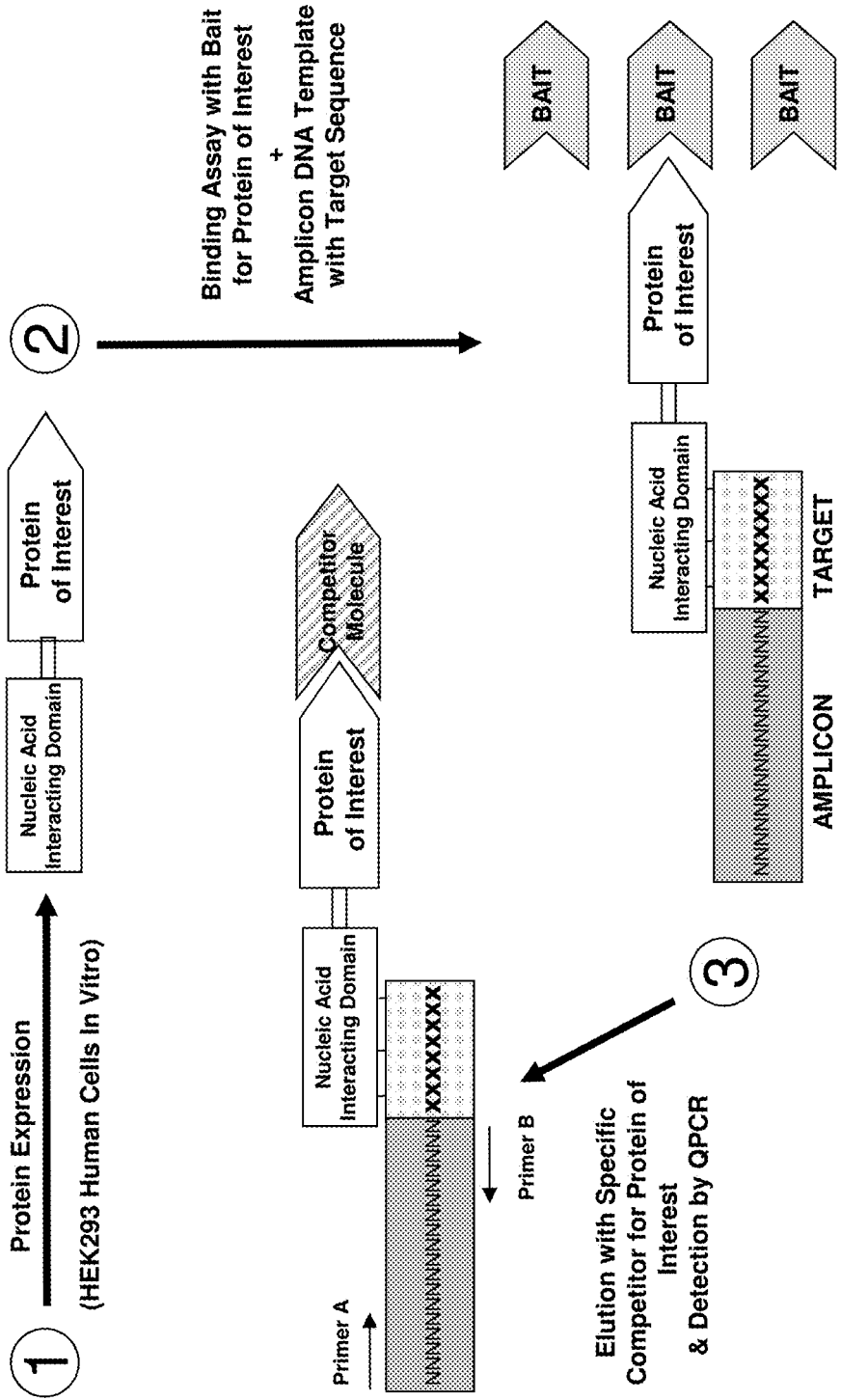
FIG. 1 is a schematic diagram depicting a competitive binding assay using a nucleic acid tag containing a PCR-amplifiable DNA sequence.

The following embodiments provided herein are exemplary and are not limitations. The methods disclosed herein have a range of applications, all of which are based on the ability to detect, quantify, or isolate a protein of interest that is tagged by a detectable nucleic acid. The compositions and methods provided herein may be used to label proteins in vitro and/or in vivo.

In some embodiments, provided herein is a nucleic acid oligomer (tag) that binds a nucleic acid-interacting motif, wherein the nucleic acid oligomer comprises (a) a first nucleic acid sequence that is a PCR amplification sequence, and (b) a second nucleic acid sequence that binds the nucleic acid-interacting motif, wherein the first nucleic acid sequence is heterologous to the second nucleic acid sequence.

In one embodiment, the length of the nucleic acid oligomer is between about 50 and about 100, about 50 and about 200, about 50 and about 300, about 50 and about 400, about 50 and about 500, about 100 and about 200, about 100 and about 300, about 100 and about 400, about 100 and about 500, about 200 and about 300, about 200 and about 400, about 200 and about 500, about 300 and about 400, about 300 and about 500, or about 400 and about 500 nucleotides in length.

As used herein, the term "about" or "approximately" means within 20%, preferably within 10%, and more preferably within 5% (or 1% or less) of a given value or range.

In some embodiments, the nucleic acid tag has a reporter function and a protein tagging function. As used herein, a "reporter" function with reference to a nucleic acid tag is the ability to be visualized or otherwise detected or quantitated. In certain embodiments, the reporter function of a nucleic acid tag comes from the radiolabeling, fluorescent labeling or biotinylation of the nucleic acid tag. As used herein, a "nucleic acid tag" is a polynucleotide, e.g., an oligomer, that binds or is capable of binding to a protein of interest, such as a protein (e.g., a kinase) fusion comprising a heterologous polynucleotide-binding domain (also called a polynucleotide-interacting motif herein), such as a DNA-binding domain (e.g., NFκB). The nucleic acid tag may be single- or double-stranded DNA, single- or double-stranded RNA, DNA-RNA hybrid, RNA-RNA hybrid, or their native or synthetic derivatives, analogs and fragments thereof. In some embodiments, the nucleic acid tag is DNA, and the reporter function label can be introduced to the DNA, for example, by any standard enzymatic reaction, such as nick translation, or by terminal labeling, with $^{32}P$, $^{125}I$ or biotin-labeled deoxynucleotide triphosphates (dNTPs), or the label can be introduced as an intercalating agent. There are many fluorescent groups that are commercially available and can be used to label the nucleic acid tag. Some examples of fluorescent labels that can be used to label the nucleic acid tag are fluorescein isothiocyante, rhodamine and coumarin and their commercial derivatives such as Texas Red® and Alexa Fluor®.

In certain embodiments, the nucleic acid tag is complexed, covalently linked or non-covalently linked to a detectable protein or polypeptide, for example, by a covalent linkage. Nucleic acid-protein fusions can be produced by any method, for example, by the method of Roberts and Szostak (U.S. Pat. Nos. 6,258,558 and 6,261,804; WO 98/31700; Roberts & Szostak (1997) Proc. Natl. Acad. Sci. USA (1997) 94:12297-12302) using a peptide acceptor, such as puromycin, as a covalent linking agent. Briefly, such an exemplary method comprises an in vitro or in situ transcription/translation protocol that generates protein covalently linked to the 3' end of its own mRNA, i.e., an RNA-protein fusion. This is accomplished by synthesis and in vitro or in situ translation of an mRNA molecule with a peptide acceptor attached to its 3' end. In specific embodiments, the peptide acceptor is puromycin, a nucleoside analog that adds to the C-terminus of a growing peptide chain and terminates translation. In one embodiment, a DNA sequence is included between the end of the message and the peptide acceptor which is designed to cause the ribosome to pause at the end of the open reading frame, providing additional time for the peptide acceptor (for example, puromycin) to accept the nascent peptide chain before hydrolysis of the peptidyl-tRNA linkage.

As used herein, a "peptide acceptor" is any molecule capable of being added to the C-terminus of a growing protein chain by the catalytic activity of the ribosomal peptidyl transferase function. In certain embodiments, such molecules contain (i) a nucleotide or nucleotide-like moiety (e.g., adenosine or an adenosine analog (di-methylation at the N-6 amino position is acceptable)), (ii) an amino acid or amino acid-like moiety (for example, any of the 20 D- or L-amino acids or any amino acid analog thereof (for example, 0-methyl tyrosine or any of the analogs described by Ellman et al., (1991) Meth. Enzymol. 202:301), and (iii) a linkage between the two (e.g., an ester, amide, or ketone linkage at the 3' or 2' position); preferably, this linkage does not significantly perturb the pucker of the ring from the natural ribonucleotide conformation. Peptide acceptors may also possess a nucleophile, which may be, without limitation, an amino group, a hydroxyl group, or a sulfhydryl group. In addition, peptide acceptors may be composed of nucleotide mimetics, amino acid mimetics, or mimetics of the combined nucleotide-amino acid structure. By a peptide acceptor being positioned "at the 3' end" of a protein coding sequence is meant that the peptide acceptor molecule is positioned after the final codon of that protein coding sequence. This term includes, without limitation, a peptide acceptor molecule that is positioned precisely at the 3' end of the protein coding sequence as well as one which is separated from the final codon by intervening coding or non-coding sequence (for example, a sequence corresponding to a pause site). This term also includes constructs in which coding or non-coding sequences follow (that is, are 3' to) the peptide acceptor molecule. In addition, this term encompasses, without limitation, a peptide acceptor molecule that is covalently bonded (either directly or indirectly through intervening nucleic acid sequence) to the protein coding sequence, as well as one that is joined to the protein coding sequence by some non-covalent means, for example, through hybridization using a second nucleic acid sequence that binds at or near the 3' end of the protein coding sequence and that itself is bound to a peptide acceptor molecule.

In addition to covalently bonded RNA-protein fusions, any other unique, PCR-amplifiable nucleic acid (for example, RNA, DNA, PNA, or any other nucleic acid which includes two or more covalently bonded, naturally-occurring or modified ribonucleotides or deoxyribonucleotides) can be coupled covalently or non-covalently to a detectable protein or polypeptide. The protein portions of the fusions are typically composed of naturally-occurring amino acid residues, but may also include amino acid analogs or derivatives, joined by peptide or peptoid bond(s).

In other embodiments, the reporter function of a nucleic acid tag is a nucleic acid sequence that is amplifiable by PCR (also referred to herein as an "amplicon"). The amplifiable sequence hybridizes or is capable of hybridizing to a PCR primer in a sequence-specific manner. In certain embodiments, the nucleic acid tag comprises a plurality of amplicons, for example, two, three, four, five, six, seven, eight, nine, ten or more amplicons. In some embodiments, the plurality of amplicons are tandem repeats of a single amplicon. In certain embodiments, the amplicon is amplifiable by quantitative PCR which permits quantification of the protein tagged by such a nucleic acid tag. In a specific amplification method, amplification of a PCR sequence includes combining the nucleic acid containing the PCR amplification template, PCR primer and qPCR probe in a standard PCR reaction mixture (generally, a mixture having a final concentration of 10 mM Tris-HCl (pH 8.3 at 25° C.), 1-4 mM $MgCl_2$, 0.1-1 mM dNTP), and treating the sample first under Hot Start conditions (for example, heating to 95° C. for 5 minutes) to minimize nonspecific annealing or mispriming, followed by a denaturation step (for example, 95° C. for 45 seconds), followed by an annealing step (55° C. for 1 minute), and followed by an extension step (72° C. for 1 minute), with up to forty rounds of the consecutive steps of denaturation, annealing and extension, to complete the amplification of the qPCR signal.

As used herein, a "protein tagging" function with reference to a nucleic acid tag is the ability to target and bind, complex, or otherwise link (e.g., covalently or non-covalently) to a nucleic acid-interacting motif, such as a fusion protein comprising (a) a protein of interest (e.g., a kinase) and (b) a heterologous polynucleotide-interacting motif, such as a DNA-binding protein (e.g., NFκB), which comprises a nucleic acid recognition sequence. The nucleic acid-interacting motif of the fusion protein binds to a nucleic acid oligomer described elsewhere herein.

In one embodiment, the target DNA sequence is a transcription factor binding site recognizable by the DNA binding domain of a transcription factor. For example, the nucleic acid tag may contain target DNA sequences recognized by DNA-binding domain of transcription factors such as NF-κB, cro repressor, lac repressor, GAL4, GCN4, LexA, Opaque-2 and TGA1a. In one embodiment, the transcription factor binding site is a naturally occurring or wildtype sequence. In another embodiment, the transcription factor binding site is a mutant sequence. In another embodiment, the transcription factor binding site may be characterized by a consensus sequence that encompasses wildtype sequences and optionally, mutant sequences. In yet another embodiment, the transcription factor binding site is a synthetic or genetically engineered sequence capable of forming a complex with either a naturally occurring, modified or synthetic DNA binding protein. In yet another embodiment, the target DNA sequence is characterized by having palindromic sequences usually recognized by protein dimers. The target sequence for Gal4 or LexA are two such examples. In yet another embodiment, the transcription factor binding site is characterized by having a GC rich region such as the target site for the transcription factor Sp1. In another embodiment, the transcription factor binding site is characterized by having a DNA-protein complex half-life of more than one, two, three, four, five or six hours with its associated DNA binding protein.

A fusion protein provided herein comprising a protein of interest and a nucleic acid-interacting motif, such as a DNA-binding protein may therefore by "tagged" by the nucleic acid oligomer provided herein through, for example, a DNA-protein complex formation. In certain embodiments, the fusion protein comprising a nucleic acid-interacting motif and a protein of interest are derived from the same organism, such as a human. In one particular embodiment, the nucleic acid tag comprises an amplicon linked to a target DNA sequence specifically recognizable by a DNA-binding protein (e.g., NFκB, cro repressor, GAL4, GCN4, LexA, Opaque-2 and TGA1a). In another embodiment, the nucleic acid tag comprises an amplicon linked to the cognate DNA sequence for the DNA-binding domain of a transcription factor. Cognate DNA sequences for such DNA-binding domains are known in the art, and exemplary sequences are provided in Table 1.

In other embodiments, a protein tagging function of a nucleic acid tag is a target DNA sequence recognized by DNA metabolizing enzyme, such as a methyltransferase, alkyltransferase and/or glycosydase. These enzymes can interact with chemically-modified DNA bases and create a covalent bond between an amino acid of the protein and the DNA sequence of the nucleic acid tag. For example, if the protein fusion contained a functional fragment of an $O^6$-alkylguanine-DNA alkyltransferase (AGT), the alkyltransferase function can be used to transfer the nucleic acid tag attached either to an $O^6$-alkylguanine or an $O^6$-benzylguanine to the AGT fusion protein to create a covalent linkage between the nucleic acid tag and the fusion protein to form a nucleic acid-protein complex (See, e.g., PCT Application No. WO02/083937). OGT can be used to label, and optionally subsequently manipulate and/or detect a protein of interest in a system in which a fusion of the protein and AGT is contacted with a labeled substrate so that the AGT transfers the label from the substrate to the AGT fusion, thereby allowing the labeled AGT-protein fusion to be manipulated and or detected by virtue of the transferred label. The label part of the substrate can be chosen by those skilled in the art dependent on the application for which the fusion protein is intended. Non-inclusive examples of labels include: (1) a spectroscopic probe such as a fluorophore, a chromophore, a magnetic probe or a contrast reagent; (2) a radioactively labeled molecule; (3) a molecule which is one part of a specific binding pair which is capable of specifically binding to a partner. Such specific binding pairs are well known in the art and include, for example, biotin, which can bind to avidin or streptavidin; (4) a molecule that are suspected to interact with other biomolecules; (5) a library of molecules that are suspected to interact with other biomolecules; (6) a molecule which is capable of crosslinking to other biomolecules as known to those skilled in the art (see, e.g., Nadeau et al. (2002) in Protein-Protein interactions: a molecular cloning manual; Ed. E Golemis, Cold Spring Harbor Laboratory Press; pp. 75-92); (7) A molecule which is capable of generating hydroxyl radicals upon exposure to $H_2O_2$ and ascorbate such as a tethered metal-chelate (see, e.g., Hori et al. (2002) in Protein-Protein interactions: a molecular cloning manual; Ed. E Golemis, Cold Spring Harbor Laboratory Press; pp. 288-311) (8) a molecule which is capable of generating reactive radicals upon irradiation with light such as malachite green (see, e.g., Jay et al. (1999) Biochim. Biophys. Acta M39-48); (9) a molecule covalently attached to a solid support, where the support may be a glass slide, a microtiter plate or any polymer in general known to those proficient in the art; (10) a nucleic acid or a derivative thereof capable of undergoing base-pairing with its complementary strand; (11) a lipid or other hydrophobic molecule with membrane-inserting properties; (12) a biomolecule with desirable enzymatic, chemical or physical properties; or (13) a molecule possessing a combination of any of the properties listed above.

As used herein, a "protein of interest" can be any conceivable polypeptide or protein that may be of interest, such as to study or otherwise characterize. In some embodiments, the protein of interest is a transferase, oxidoreductase, hydrolase, ligase, isomerase or lyase. In one embodiment, the protein of interest is a human polypeptide or protein. In certain embodiments, the protein of interest is a transferase having transferase activities, such as an acyltransferase, glycosyltransferase, amidotransferase or sulfurtransferase. In another embodiment, the protein of interest is a hydrolase, peptidase, protease or phosphatase.

In certain embodiments, the kinase is a lipid kinase, such as a lipid kinase of the P13K family (e.g., mTOR). In specific embodiments, the protein of interest is a protein kinase (see, e.g., Manning (2002) Science 298:1912). In specific embodiments, the protein of interest is a tyrosine kinase, or a serine/threonine kinase. In some embodiments, the protein of interest is a human non-receptor tyrosine kinase, for example, a non-receptor tyrosine kinase that is a member of the ABL, ACK, CSK, MATK, FAK, PYK2, FES, FRK, JAK, SRC-A, SRC-B, TEC, and/or SYK families. In other embodiments, the protein of interest is a human receptor tyrosine kinase, for example, a receptor tyrosine kinase that is member of the ALK, AXL, DDR, EGFR, EPH, FGFR, INSR, MET, MUSK, PDGFR, PTK7, RET, ROR, ROS, RYK, TIE, TRK, VEGFR, AATYK, and/or SuRTK106 families.

In some embodiments, a protein of interest is a transmembrane protein, such as a 7-transmembrane helix protein, such as a G-protein coupled receptor (GPCR). A protein of interest may also be transmembrane ion channel protein, and in certain embodiments, a ligand gated ion channel protein. In other embodiments, a protein of interest is a nuclear hormone receptor protein, such as a classic steroid hormone receptor and/or a receptor in the orphan class of nuclear hormone receptors.

In yet other embodiments, a protein of interest is an extracellular signaling molecule or factor, such as a cytokine (e.g., an interferon and/or an interleukin), growth factor, and/or hormone (e.g., insulin, glucagon or prostaglandins). In certain embodiments, a protein of interest is a protein involved in intracellular signal cascades, such as an enzyme or cofactor involved in phosphatidinyl-inositol signaling, cAMP, or cGMP generation.

In some embodiments, a protein of interest is an antibody, small chain variable fragment (scFv), antigen or epitope.

The protein of interest can, in some embodiments, be the expression of a nucleotide sequence generated by random mutation, the expression of a nucleotide sequence containing systematically synthesized sequences, or it may be an expressed cDNA. In one example, the protein of interest being studied or characterized is derived from a human cDNA library (i.e., a human protein).

In certain embodiments, the protein of interest is a chimeric fusion between a protein of interest and a heterologous DNA-binding protein. In such chimeric fusions, at least two gene sequences representing each half of the chimera can be fused in-frame, cloned into the appropriate vector and expressed in a host cell of choice. In certain embodiments, the protein of interest is 5' of the nucleotide-binding domain (e.g., DNA-binding protein). In other embodiments, the protein of interest is 3' of the nucleotide-binding domain (e.g., DNA-binding protein). In specific embodiments, the protein of interest and/or the nucleotide-binding domain (e.g., DNA-binding protein) retain the respective activity of the wildtype protein. The protein of interest, including chimeric fusions, may be expressed in any of a variety of host cells, including bacterial, insect, mammalian or plant host cells. When the protein of interest is expressed in the appropriate eukaryotic host cell, it can exhibit post-translational eukaryotic modification that is present in native protein and is therefore expected to have the structure and function of a native protein. Alternatively, the protein of interest may be otherwise synthetically linked (e.g., using a polypeptide linker) to the nucleotide-binding domain Also provided herein is a library of fusion proteins, comprising a plurality of fusion proteins provided herein, wherein at least two or more of the fusion proteins differ from each other. In certain embodiments, provided herein is a library of oligomers, comprising a plurality of oligomers provided herein, wherein at least two or more of the oligomers differ from each other. Also provided herein is a nucleic acid encoding a fusion protein provided herein, as well as a vector comprising a nucleic acid encoding a fusion protein provided herein. Additionally, provided herein is a host cell comprising a vector comprising a nucleic acid encoding a fusion protein provided herein. In certain embodiments, the host cell is a bacterial, insect, mammalian or plant host cell.

In certain embodiments, also provided herein is a functional assay which studies the activity of the protein of interest. In some embodiments, the activity of a protein of interest is assessed using a nucleic acid tag, such as by detecting the presence of the nucleic acid tag. Such a functional assay may be used to study the effects of test compounds as inhibitors, agonists, antagonists or more generally, as modulators, of protein activity.

The protein of interest can be a chimera comprised of (a) a nucleic acid interacting motif and (b) the protein being studied or characterized (the portion of the protein that is the true "protein of interest"). In one embodiment of the invention, the nucleic acid recognition motif may be a DNA-binding protein. Exemplary motifs are shown in Table 1. DNA-binding protein may include the DNA-binding domain of transcription factors, including transcriptional activators and repressors. Examples of suitable DNA-binding domains include NF-κB (eukaryotic), cro repressor (λ bacteriophage), lac repressor (yeast), GAL4 (yeast), GCN4 (yeast), Lex-A (*E. coli*), Opaque-2 (maize) and TGA1a (tobacco). Suitability of the DNA-binding domain may also depend of the association times of a particular DNA-binding domain to its target sequence. For example, NF-κB is considered to form a strong association with its target DNA sequence, with a dissociation half-life of over 4 hours. (See Speight et al. (2001) *Chem. Biol.* 8:951-965). Suitable DNA-binding domains also include synthetic DNA-binding domains constructed by combining different pieces of naturally occurring and/or engineered DNA-binding motifs, such as synthetic zinc fingers, leucine zippers, winged helix, helix-loop-helix, homeodomain and POU domain. The chimeric protein may be "tagged" through the recognition of the DNA-binding-domain to a certain binding recognition sequence of the nucleic acid tag. In another embodiment of the invention, the nucleic acid recognition motif may be a full-length, partial-length or a functional fragment of a DNA-metabolizing enzyme already mentioned above, such as DNA ligases, DNA repair enzymes, restriction enzymes or DNA methyltransferases.

TABLE 1

Exemplary Nucleic Acid Tag, Binding Domain and Binding Domain Recognition Motif Sequences

| Nucleic acid tags for NF-κB binding | TTGTGAATTGCTGACCGTAGATGTCAACTTTGACCATC AGACAACGTTTCTCCATTCCAATTATGCGAGAATCCT<u>A</u> <u>GGGAATTCCCC</u>TAGATCGCATG (SEQ ID NO: 1); amplicon sequence is the sequence preceding the underlined region, the NFκB recognition sequence is the underlined region. CGGCGTAAAAACGAATACCATGTCTCTCATCGCTCGAC TCATTCTTTCCAAAATTTCGCGGAACCAGG<u>GGGAATTC</u> <u>CCC</u>TAGATCGCATG (SEQ ID NO: 2); amplicon sequence is the sequence preceding the |

TABLE 1-continued

Exemplary Nucleic Acid Tag, Binding Domain and Binding Domain Recognition Motif Sequences

| | |
|---|---|
| | underlined region, the NFκB recognition sequence is the underlined region AAACAATGAGACACCAGGGATTAGATATCAGTACAATG TGCTTCCACA AAGGATCACCAGCAATATTCCAAA<u>GGGAATTCCC</u>CTAG ATCGCATG (SEQ ID NO: 3); amplicon sequence is the sequence preceding the underlined region, the NFκB recognition sequence is the underlined region |
| Nucleic acid tag for GAL4 binding | CATGCGACAGCGGAGTTACGTCCAGAAGGACAACATC TTTGACATCGCCTCTTGAATTGCTGCACCAAGGGCTAC TGCCGGAGTACTGTCCTCCGCTAGATCGCATG (SEQ ID NO: 4); amplicon sequence is the sequence preceding the underlined region, the GAL4 recognition sequence is the underlined region. |
| NF-κB DNA binding domain | MAGPYLQILEQPKQRGFRFRYVCEGPSHGGLPGASSEK NKKSYPQVKICNYVGPAKVIVQLVTNGKNIHLHAHSLVGK HCEDGICTVTAGPKDMVVGFANLGILHVTKKKVFETLEAR MTEACIRGYNPGLLVHPDLAYLQAEGGGDRQLGDREKEL IRQAALQQTKEMDLSVVRLMFTAFLPDSTGSFTRRLEPVV SDAIYDSKAPNASNLKIVRMDRTAGCVTGGEEIYLLCDKV QKDDIQIRFYEEEENGGVWEGFGDFSPTDVHRQFAIVFK TPKYKDINITKPASVFVQLRRKSDLETSEPKPFLYYPEIKD KEEVD (SEQ ID NO: 5) |
| GAL4 DNA binding domain | MKLLSSIEQACDICRLKKLKCSKEKPKCAKCLKNNWECR YSPKTKRSPLTRAHLTEVESRLERLEQLFLLIFPREDLDMI LKMDSLQDIKALLTGLFVQDNVNKDAVTDRLASVETDMPL TLRQHRISATSSSEESSNKGQRQLTVS (SEQ ID NO: 6) |
| NFκB recognition sequence | GGGAATTCCC (SEQ ID NO: 7) |
| NF-κB recognition sequence | GGGAAATTCCC (SEQ ID NO: 8) |
| NF-κB recognition sequence | GGGACTTTCC (SEQ ID NO: 9) |
| NF-κB consensus sequence | GGGRNNYYCC (SEQ ID NO: 10) (R = purine; Y = pyrimidine) (N = any nucleotide) |
| Gal4 recognition sequence | CGGAGTACTGTCCTCCG (SEQ ID NO: 11) |
| Gal4 consensus sequence | CGGNNNNNNNNNNNCCG (SEQ ID NO: 12) (N = any nucleotide) |
| ReIA/c-ReI consensus sequence | HGGARNYYCC (SEQ ID NO: 13) (H = A,C or T; R = purine; Y = pyrimidine) |
| Cro repressor recognition sequence | TCTATCACCGCGGGTGATAAA (SEQ ID NO: 14) |
| Lac repressor recognition sequence | GAATTGTGAGCGCTCACAATT (SEQ ID NO: 15) |
| GCN4 recognition sequence | AGTGACTCAT (SEQ ID NO: 16) |
| Opaque-2 recognition sequence | TGTCATTCCACGTAGATGAAAA (SEQ ID NO: 17) |
| Opaque-2 recognition sequence | TCCACGTAGA (SEQ ID NO: 18) |
| Lex-A recognition sequence | CTGTATATATATACAG (SEQ ID NO: 19) |
| TGA1a recognition sequence | GACGTC (SEQ ID NO: 20) |
| EGR-1 or Zif 268 recognition sequence | GCGTGGGCGT (SEQ ID NO: 21) |

In vitro methods provided herein include using a nucleic acid tag to visualize one or more proteins for the study of subcellular localization of the labeled proteins, for the study of labeled organelles, for the monitoring of the movement of labeled proteins including translocation, internalization or secretion of proteins, and/or for the monitoring of spatial and temporal expression profiles of labeled proteins.

Other methods provided herein comprise the use of a nucleic acid tag for detecting, quantifying and/or sorting labeled protein using flow cytometry. In such an application, the nucleic acid tag can, in certain embodiments, be fluorescently labeled for fluorescent-activated cell sorting (FACS).

In yet other methods provided herein, a nucleic acid tag is biotinylated, which permits the detection of the protein of interest by immunological methods. Alternatively, purification of the labeled protein of interest may be achieved by affinity chromatography.

In other methods provided herein, a nucleic acid tag is immobilized in an array. Such an array can be used in certain embodiments to create an addressable protein array, such as for a protein expression profiling analysis.

In one embodiment, provided herein is a method for identifying a protein of interest that binds to a ligand, comprising (i) contacting the ligand with a fusion protein comprising (a) a first domain comprising the protein of interest, and (b) a second domain comprising a nucleic acid-interacting motif, wherein the protein of interest and the nucleic acid-interacting motif differ from each other (e.g., different proteins from the same organism or different proteins from different organism); (ii) adding a nucleic acid oligomer comprising a nucleic acid sequence that binds the nucleic acid-interacting motif of the fusion protein; (iii) removing unbound nucleic acid oligomer and/or unbound fusion protein; and (iv) detecting whether the nucleic acid oligomer is bound to the fusion protein; whereby detection of bound nucleic acid oligomer indicates the protein of interest binds to the ligand.

The methods and assays provided herein can be practiced in any order. For example, in certain embodiments, the nucleic acid tag is contacted with the fusion protein before, during (e.g. simultaneously), or after contact of the fusion protein with the reference ligand. In certain embodiments of the methods provided herein, the nucleic acid oligomer is contacted with a nucleic acid-interacting motif under conditions in which the nucleic acid-interacting motif binds to the oligomer.

In another embodiment, provided herein is a method of identifying a test compound that binds to a protein of interest, comprising (i) in the presence and absence of test compound, contacting an immobilized reference ligand, which binds the protein of interest, with a fusion protein comprising (a) a first domain comprising the protein of interest, and (b) a second domain comprising a nucleic acid-interacting motif, wherein the protein of interest and the nucleic acid-interacting motif differ from each other; (ii) adding a nucleic acid oligomer comprising a nucleic acid sequence that binds the nucleic acid-interacting motif of the fusion protein; (iii) removing unbound nucleic acid oligomer and/or unbound fusion protein; and (iv) detecting whether the nucleic acid oligomer is bound to the fusion protein; wherein a reduction in the amount fusion protein bound to the immobilized reference ligand in the presence of test compound as compared to the absence of test compound indicates the test compound binds the protein of interest.

In some embodiments, provided herein is a method of identifying a test compound that binds to a protein of interest, the method comprising: (i) contacting a fusion protein to an oligomer under conditions wherein said fusion protein binds to said detectable oligomer, wherein said fusion protein comprises said protein of interest is fused to a nucleic acid interacting motif, and wherein said detectable oligomer comprises a nucleic acid sequence that binds to said nucleic acid-interacting motif, (ii) contacting the mixture in step (i), to an immobilized reference ligand capable of binding said protein of interest, in the presence and in the absence of said test compound; (iii) removing unbound oligomer and/or unbound fusion protein; (iv) quantifying the fusion protein bound to the immobilized reference ligand by detecting said nucleic acid oligomer; wherein a reduction in the amount of fusion protein bound to the immobilized bait in the presence of compound as compared to the absence of compound indicates that said test compound binds to said protein of interest.

In another embodiment, provided herein is a method of identifying a test compound that binds to a protein of interest, the method comprising (i) contacting a fusion protein to an oligomer under conditions wherein said fusion protein binds to said oligomer, wherein said fusion protein comprises said protein of interest fused to a nucleic acid interacting motif, and wherein said oligomer comprises a PCR amplification sequence and a nucleic acid sequence that binds to said nucleic acid-interacting motif, (ii) contacting the mixture in step (i), to an immobilized reference ligand capable of binding said protein of interest, in the presence and in the absence of said test compound; (iii) removing unbound oligomer and/or unbound fusion protein; (iv) detecting or quantifying the fusion protein bound to the immobilized reference ligand by qPCR; wherein a reduction in the amount of fusion protein bound to the immobilized bait in the presence of compound as compared to the absence of compound indicates that said test compound binds to said protein of interest.

In specific embodiments, a nucleic acid tag is employed in a screening assay to identify from a large number of candidate ligands (or "test compounds"), those ligands that will competitively bind to the protein of interest, in the presence of a competing reference ligand that is known to bind to the protein of interest. Candidate test compounds may include one or more organic chemical compounds, inorganic chemical compounds, synthetic nucleic acids, natural nucleic acids, synthetic polypeptides, natural polypeptides, peptide fragments and/or proteins. Likewise, the competing reference ligand may be organic chemical compounds, inorganic chemical compounds, synthetic nucleic acids, natural nucleic acids, synthetic polypeptides, natural polypeptides, peptide fragments and/or proteins.

For example, in a screen for a pharmaceutical compound, one or more test compounds, which can be free in solution, are evaluated for an ability to compete with an immobilized reference ligand or "bait" for binding a protein of interest. In certain embodiments, the immobilized reference ligand is a pharmaceutical compound. In specific embodiments, baits may be selected based on their promiscuity rather than selective interaction with a plurality of proteins of interest. In some embodiments, the baits are selected such that the bait binds to two, three, four, five, ten, fifteen, twenty, thirty, forty, fifty or more proteins of interest, such as when the bait is used against a panel or library comprising a plurality of proteins of interest.

In one embodiment, the screen is for a kinase inhibitor (or other modulator). The immobilized reference can be any known inhibitor or other binder of a kinase. In embodiments, in which competitive binding assays for a panel of kinases is created, baits may be selected based on their promiscuity rather than selective interaction with multiple kinases. Exemplary baits having promiscuity profiles are known, such as SB202190, staurosporine, purvalanol B, SU5402, imatinib mesylate, SU6668, Iressa and PD-173955. Techniques for immobilizing such reference compounds are known, see, e.g., U.S. Publication No. 20050153371 (e.g., Example 11). As used herein, a "solid support" is, without limitation, any column (or column material), bead, test tube, microtiter dish, solid particle (for example, magnetic, agarose or sepharose beads), microchip (for example, glass, fiberglass, latex, silicon, silicon-glass, or gold chip), or membrane (for example, the membrane of a liposome or vesicle). a plastic material (for example, polystyrene or polyvinylchloride, or sensor chip (for example, those used with a BIAcore system) to which a ligand, such as a reference ligand, may be bound, either directly or indirectly (for example, through other binding partner intermediates such as other antibodies or Protein A), or in which a ligand, such as a reference ligand may be embedded (for example, through a receptor or channel).

The reference ligand (bait) can be captured using any standard procedure, for example, by biotinylation of the reference ligand, followed by capture of biotinylated reference ligand using immobilized streptavidin (for example, streptavidin immobilized on magnetic beads or a column). Proteins of interest that bind to the reference ligand (and nucleic acid tags, which bind to the proteins of interest) will remain bound to the solid support, while unbound binding reagents (proteins of interest and/or nucleic acid tags) are washed away. Following capture of bound protein of interest, a nucleic acid tag that has bound a target in the sample (e.g., or protein of interest of a panel of proteins of interest) is detected simply by performing a PCR reaction using primers which hybridize to the amplicon portion of the nucleic acid tag. In certain embodiments, the PCR reaction is carried out using standard quantitative methods (for example, using Taq Man by Perkin-Elmer). In some embodiments, multiple protein of interest-nucleic acid tag complexes are retained by the solid support, in which case the individual members of the isolated pool can be identified, such as through the amplification of each unique nucleic acid tag, which is specific for a particular protein of interest, e.g., in a panel.

In one embodiment, the immobilized reference ligand binds to the ATP-binding site of a kinase, and the screen enables the identification of compounds that competitively bind to the ATP-binding site of the kinase.

In another embodiment, the immobilized reference binds to a site comprising the ATP-binding site and a site adjacent to or adjoining the ATP-binding site. Such a reference "bait" may be used to determine whether a test compound binds in an ATP-competitive or non ATP-competitive manner, such as by running a competitive binding assay in the presence or absence of ATP and determining the effect of ATP on the apparent $K_d$ of the test compound to the kinase. In the situation where the test compound binds to the ATP-bound kinase in a cooperative fashion, a test compound that is ATP-competitive will display an upward shift in apparent $K_d$ in the presence of ATP, while a test compound that is non-ATP competitive will show either no change in apparent $K_d$ or, in the situation where the test compound and ATP binds cooperatively, a downward shift in apparent $K_d$ in the presence of ATP.

In other embodiments, provided herein is a method of identifying a test compound that binds to a protein of interest having an ATP-binding site, wherein said test compound is a non-ATP competitive binder to the protein of interest, the method comprising (a) in (i) the presence and absence of test compound, and (ii) in the presence and absence of exogenous ATP; contacting an immobilized reference ligand, which binds the protein of interest, with a fusion protein comprising a first domain comprising the protein of interest, and a second domain comprising a nucleic acid-interacting motif, wherein the protein of interest and the nucleic acid-interacting motif differ from each other; (b) adding a nucleic acid oligomer comprising a nucleic acid sequence that binds the nucleic acid-interacting motif of the fusion protein; (c) removing unbound nucleic acid oligomer and/or unbound fusion protein; and (c) detecting whether the nucleic acid oligomer is bound to the fusion protein; wherein (i) a reduction in the amount fusion protein bound to the immobilized reference ligand in the presence of test compound and absence of ATP, as compared to the absence of test compound and absence of ATP, indicates the test compound binds the protein of interest, and wherein (ii) an increase in the amount of nucleic acid oligomer bound to the fusion protein in the presence of test compound and presence of ATP. as compared to the presence of test compound and the absence of ATP, indicates that the test compound is a non-ATP competitive binder to the protein of interest.

In one embodiment, provided herein is a method of identifying a test compound that binds to a protein of interest in a non-ATP competitive manner, the method comprising (i) contacting a fusion protein to a detectable oligomer under conditions wherein said fusion protein binds to said oligomer, said fusion protein comprising (a) a first domain comprising the protein of interest and (b) a second domain comprising a nucleic acid interacting motif, and said oligomer comprising a nucleic acid sequence that binds to said nucleic acid-interacting motif; (ii) contacting the mixture in step (i) to an immobilized reference ligand, in the presence of varying concentrations of said test compound and in the absence of said test compound, wherein said immobilized reference ligand binds to the fusion protein at the ATP-binding site and to a region (e.g., outside the ATP-binding site) adjacent or adjoining the ATP-binding site, (iii) removing unbound nucleic acid oligomer and/or unbound fusion protein; and (iv) quantifying the amount of fusion protein bound to the immobilized reference ligand by detecting the oligomer at each concentration of test compound (e.g., to obtain a binding curve); (v) determining the concentration of said test compound at which the amount of protein of interest bound to the immobilized ligand is 50% of the amount of protein of interest bound to the immobilized ligand in the absence of compound wherein said concentration is the $K_d$ said test compound; and (vi) repeating steps (i)-(v) wherein the mixture at step (ii) is further contacted with ATP; wherein said test compound binds to said fusion protein in a non-ATP competitive manner when the calculated $K_d$ in the presence and in the absence of ATP remains unchanged or when the calculated $K_d$ in the presence of ATP is less than the calculated Kd in the absence of ATP. In certain embodiments, the nucleic acid oligomer comprises an amplicon, and detection further comprises qPCR.

In yet another embodiment, the immobilized reference binds to a site that is adjacent to, or adjoining the ATP binding site, and which optionally overlaps with the ATP-binding site. Such a binding site may either encompass the substrate binding site, or may lie outside of the substrate binding site. If a reference molecule binds to the kinase at a site encompassing the substrate binding site, such a reference "bait" may be used to determine whether a test compound binds to the kinase in a substrate-competitive or non substrate-competitive manner, by running a competitive binding assay in the presence or absence of substrate and determining the effect of substrate on the apparent $K_d$ of the test compound to the kinase. A test compound that is substrate-competitive will display an upward shift in apparent $K_d$ in the presence of substrate, while a test compound that is non-substrate competitive will show either no change in apparent $K_d$ or, where the test compound and substrate binds cooperatively, a downward shift in apparent $K_d$ in the presence of substrate. A test compound may be run through such a competitive binding assay in a secondary screen, when the test compound has already been determined to be a non-ATP competitive molecule from the assay described herein.

In certain embodiments, the concentration of test compound required to displace the protein of interest from the immobilized reference ligand or "bait" is a measure of its affinity to the protein of interest. If the protein of interest contains a DNA-binding domain, the amount of protein of interest retained on solid support may be detected by a nucleic acid tag containing a sequence capable of forming a complex with the DNA-binding domain (as a fusion with the protein of interest). The nucleic acid tag may be detectable by radiolabeling, fluorescent labeling or by amplification of a PCR amplification sequence as described above.

Thus, provided herein is a method of identifying a compound that binds to a protein of interest (e.g., a chimeric fusion), comprising contacting a protein of interest to a reference ligand "bait" immobilized on solid support in the presence and absence of at least one candidate test molecule in solution, titrating the amount of protein of interest retained by the support with increasing concentrations of test molecule starting at a concentration of zero, adding to the mixture a detectable nucleic acid tag to label the protein of interest and determining the amount of immobilized protein of interest for each concentration of test compound. A reduction in the amount of bound protein of interest in the presence of test molecule compared to the absence of test molecule identifies the test molecule as binding to the protein of interest. In a "forward screen," large numbers of test compounds can be screened rapidly to identify those which will bind to a protein of interest. The affinity with which the alternative, competitor molecule binds the protein can also be preselected by adjusting the concentration of test compound. If higher affinity is desired, lower concentrations of the candidate are offered and success in dislodging the protein of interest from an immobilized reference ligand is required at these lower concentrations. The reference ligand can be a target molecule which has been identified or is known to bind to a particular protein of interest. This reference ligand can be immobilized to solid support using any conventional method as described herein. The immobilized reference ligand can then be contacted with a one or a plurality of proteins of interest to which the reference ligand is known to bind. In certain embodiments, this interaction is tested in a sample which contains at least one test compound and a sample which contains no test compound. The detectable nucleic acid tag provided herein may then be used to determine the amount of protein bound to the immobilized reference ligand in the presence and absence of test compound. Successfully binding test compounds will decrease the amount of protein of interest bound to the reference ligand as compared to the absence of test compound.

This approach offers the ability to screen large numbers of test compounds rapidly by conducting the initial competition reactions supplying the test compounds in pools. The number of candidates in each pool is arbitrary but may be 2, 5, 10, 50, or even more. If the pool is unsuccessful in lowering the amount of bound protein of interest, no member of the pool need further be tested. If the pool is successful, individual test compounds present in the pool can be tested, or intermediate size pools of those originally used can be employed. For example, if the initial pool contains 50 test compounds, the testing can be continued with 5 pools each containing 10 of the 50 test compounds. Only successful pools are then further subdivided for subsequent rounds of testing. The competition binding screen is disclosed in further detail in, e.g., Fabian et al. (2005) Nature Biotechnology 23(3), 329-336 and U.S. Publication Nos. 2003/0186221; 2004/0009470, and 2005-0009099; each of which are incorporated by reference herein.

In another method provided herein, the dissociation constant of the test molecule may be determined when certain assay conditions are met: firstly, that the concentration of the protein of interest is kept low enough such that the concentration of protein is less than the $K_d$ of the test molecule for the protein of interest, and secondly, that the concentration of the immobilized reference ligand is less than the $K_d$ of the reference ligand for the protein of interest ($K_{ref}$).

To satisfy the first condition, the concentration of the protein of interest in the assay is kept quite low, typically less than 0.1 nM. When a test compound is expected to be a very tight binder of the protein of interest, the protein of interest is diluted to a lower concentration. There is no excess of protein in the binding experiment and the protein concentration is kept at a concentration lower than the $K_d$ of the test molecule for the protein of interest.

The second condition must be satisfied because the apparent $K_d$ for the test compound will be affected by the $K_d$ of the reference ligand for the protein of interest ($K_{ref}$) only when the concentration of the immobilized reference ligand is greater than $K_{ref}$. To satisfy this second condition, the competitive binding assay is run using a concentration of the immobilized reference ligand falling in the range of 0.3 nM-300 nM, which is in the general range of $K_{ref}$ (i.e. the $K_d$ of the reference molecule to the protein of interest). When these conditions are met, competitive binding can be described by the equation:

$$f/f_0 = K_{comp}/(K_{comp}+[comp])$$

where f is the fraction of protein of interest bound to the immobilized reference ligand in the presence of the competitor test molecule in solution; $f_0$ is the fraction bound in the absence of dissolved test molecule; $K_{comp}$ is the equilibrium dissociation constant ($K_d$) for the interaction between the protein of interest and the competitor test molecule in solution; and where [comp] is the concentration of the competitor test molecule in solution. The number of protein of interest bound to the reference ligand as a function of the test molecule concentration may be plotted on a graph and the $K_d$ calculated by fitting the curve to the binding equation $f/f_0=(L+(H-L))\times(K_{comp}/(K_{comp}+[comp]))$, where L is the lower baseline, H is the upper baseline, $K_{comp}$ the binding constant for the interaction between the test molecule and the protein of interest, and [comp] the concentration of test molecule. At 50% competition, the fraction of bound protein in the presence of test molecule is one half of that in the absence of test molecule, or $f/f^0=\frac{1}{2}$ and $K_{comp}$ is equal to [comp].

A method of determining the $K_d$ value of a test compound for a protein of interest, comprising (i) in the presence of varying concentrations and absence of test compound, contacting an immobilized reference ligand, which binds the protein of interest, with a fusion protein comprising (a) a first domain comprising the protein of interest, and (b) a second domain comprising a nucleic acid-interacting motif, wherein the protein of interest and the nucleic acid-interacting motif differ from each other; (ii) adding a nucleic acid oligomer comprising a nucleic acid sequence that binds the nucleic acid-interacting motif of the fusion protein; (iii) removing unbound nucleic acid oligomer and/or unbound fusion protein; and (iv) obtaining a competitive binding curve by detecting or otherwise quantitating the nucleic acid oligomer that is bound to the fusion protein retained on the solid support at each of the varying concentrations and absence of test compound; whereby the $K_d$ value of the test compound for the protein of interest is the concentration at which the protein of interest retained by the immobilized reference ligand in the presence of test compound is 50% of the protein of interest retained in the absence of test compound.

Using the screening assays provided herein, a test compound may be tested against a panel of proteins of interest to generate a $K_d$ profile of the test compound for that particular panel. The $K_d$ profile is useful for determining whether or not a compound has target specificity, a feature which may be useful when a target belongs to a family of proteins sharing, as an example, similar substrate binding sites, where there is a great potential for compound cross-reactivity.

Any of the screening assays described herein can be run in either singleplex or multiplex format. In one exemplary multiplex format, a test compound is screened and tested for its binding properties against multiple proteins from a panel of proteins of interest simultaneously. Where multiple proteins of interest are being assayed simultaneously or sequentially, nucleic acid tags unique to each protein of interest (e.g., different amplicons) can be used to distinguish the different proteins. For example, where the nucleic acid tag contains a PCR amplification marker, the PCR amplification marker would be unique to the particular protein of interest to be detected. Each protein can therefore be tagged by a nucleic acid tag comprising a DNA target sequence and a PCR amplification marker that are each unique to the protein of interest. In this particular format, because each nucleic acid tag binds uniquely to a specific protein, the proteins of interest may be pooled either at the competition binding step and/or pooled at the elution step after the competition binding step has been performed individually for each protein. Fractions from the pool may then be assayed for individual protein interaction to the test compound.

Alternatively, if the proteins of interest being assayed together in the multiplexed format are comprised of the same nucleic acid-interacting protein (e.g., NFκB), the nucleic acid tags can contain the same DNA target sequence, but unique reporters, such as unique PCR amplification markers that can be used to distinguish the different proteins of interest. In this alternative embodiment, a nucleic acid interacting protein having a high affinity for its cognate DNA and/or a long protein-DNA complex half-life could be selected. In one embodiment, NF-κB is selected for its high affinity to its cognate DNA (see Table 1) and its long complex half life of 4-40 hours. In such an embodiment, the chimeric fusion protein of interest would comprise the protein of interest and the DNA-binding domain of NF-κB. In this alternative embodiment of the multiplex format, the competition binding step may be carried out by first "pre-loading" each fusion protein with a nucleic acid tag containing an amplicon unique to each fusion protein, and running the competition binding in a multiplex format by combining, e.g., two "pre-loaded" kinases or up to six (or more) "pre-loaded" fusion proteins into a common vessel.

In certain embodiments, provided herein is a method of simultaneously identifying a test compound that binds to two or more proteins of interest, comprising (i) in the presence and absence of test compound, contacting an immobilized reference ligand, which binds each of the two or more proteins of interest, with two or more fusion proteins, wherein each fusion protein independently comprises (a) a first domain comprising only one of the two or more proteins of interest, and (b) a second domain comprising a nucleic acid-interacting motif, wherein the protein of interest and the nucleic acid-interacting motif differ from each other; (ii) adding two or more nucleic acid oligomers, wherein each of the two or more nucleic acid oligomers comprises a nucleic acid sequence that independently binds the nucleic acid-interacting motif of only one of the two or more fusion proteins; (iii) removing unbound nucleic acid oligomer and/or unbound fusion protein; and (iv) detecting or otherwise quantitating each of the two or more nucleic acid oligomers; wherein a reduction in the amount of two or more fusion proteins bound to the immobilized reference ligand in the presence of test compound as compared to the absence of test compound indicates the test compound binds the respective two or more proteins of interest.

A method of simultaneously determining the $K_d$ value of a test compound for two or more proteins of interest, comprising (i) in the presence of varying concentrations and absence of test compound contacting an immobilized reference ligand, which binds each of the two or more proteins of interest, with two or more fusion proteins, wherein each fusion protein independently comprises (a) a first domain comprising only one of the two or more proteins of interest, and (b) a second domain comprising a nucleic acid-interacting motif, wherein the protein of interest and the nucleic acid-interacting motif differ from each other; (ii) adding two or more nucleic acid oligomers, wherein each of the two or more nucleic acid oligomers comprises a nucleic acid sequence that independently binds the nucleic acid-interacting motif of only one of the two or more fusion proteins; (iii) removing unbound nucleic acid oligomer and/or unbound fusion protein; and (iv) obtaining a competitive binding curve by detecting or otherwise quantitating each of the two or more nucleic acid oligomers that is bound to the two or more fusion proteins retained on the solid support at each of the varying concentrations and absence of test compound; whereby the $K_d$ value of the test compound for each of the two or more proteins of interest is the concentration at which each of the two or more proteins of interest retained by the immobilized reference ligand in the presence of test compound is 50% of the respective two or more proteins of interest retained in the absence of test compound.

In another embodiment, a silent decoy nucleic acid tag may be added to the common vessel before the binding step is carried out. The silent decoy may be a nucleic acid tag comprising the DNA target sequence (e.g., a cognate NFκB DNA sequence) recognized by the common nucleic-acid interacting protein (e.g., NFκB), but which lacks any sort of reporter function. If the reporter function used in this alternative embodiment is qPCR amplification, the silent decoy may be a "qPCR-silent" decoy lacking any sort of PCR amplification sequence and therefore does not produce any signal at the qPCR step. Such a decoy would be added in the case where the nucleic acid interacting protein binds reversibly to its cognate DNA, as in the case where the nucleic acid interacting protein is the DNA-binding domain of a transcription factor. The purpose of such a decoy would be to minimize the scramble of signal that would result from the exchange of the nucleic acid tags between different fusion proteins, by increasing the likelihood that any exchange between tags would involve a "silent" decoy tag rather than an exchange between two tags and that any exchange would therefore reduce the binding signal for a particular protein rather than scramble it.

In certain embodiments of the multiplex assay, the binding signal is read individually for each protein of interest (e.g., a kinase) by aliquoting out the eluates from the binding assay into individual vessels and assaying each aliquot by qPCR. Alternatively, the binding signal may be determined in a multiplexed format by aliquoting the samples from the binding assay such that each sample is assayed for two or three or more different signals in the same sample, for example, by multiplexed qPCR. In another embodiment of the multiplex format, the multiplexing may occur only at the readout step, where the binding signal is being measured. In such an embodiment, the competition binding step is run individually for each protein of interest, and then pooled at the elution step, where each fraction of the pool may be assayed for individual protein interaction to the test compound.

The panel of proteins tested in the multiplex format may or may not belong to the same family of proteins. In one embodiment, the panel of proteins comprises kinases, such as kinases of the receptor tyrosine kinase family.

In another embodiment of a multiplex format, multiple test compounds are tested simultaneously with a protein of interest, to determine the degree to which the test compounds compete with the reference ligand for binding the protein of interest. Multiplexing in this manner permits rapid screening of large test compound libraries. Only certain test compound pools exhibiting the desired range of competitive binding need to be examined further to identify the specific compound having the desired binding affinity to the protein of interest.

A $K_d$ profile of a test compound and/or protein of interest may be entered into a database or other tabular form for ease of use and subsequent analysis. In one data format, the identities of the screened test compounds are displayed in rows of a table, the identities of the proteins of interest are displayed in columns, and each cell of table contains the dissociation constant values of each protein for each test compound. Each row of the table therefore represents a specificity profile of a test compound for the protein panel and readily permits the identification and selection of test compounds exhibiting selective binding, over those test compounds exhibiting promiscuous binding to multiple proteins. Computer-based clustering methods can also be used to represent the data in such a way that the binding profile of every test molecule and every protein of interest can be related to one another. In one example of a clustered representation of the data, proteins that tend to bind the same test molecules are placed close to on another, whereas proteins that tend to bind different test molecules are placed far apart. An indication of where a test compound binds in a cluster map provides additional insight that may be valuable for making predictions for the structure-activity relationship of a compound family.

The screening assays provided herein allow numerous advantages over other screening formats. For example, the screened test compound does not need to be immobilized or chemically modified in any way, and therefore is immediately available for scale-up, multiplexing and high throughput screening, allowing the test molecule(s) to be tested both rapidly and broadly. In addition, since the competitive binding assay uses highly sensitive detection methods (e.g., qPCR), it requires less amounts of scarce and costly materials such as recombinant proteins. Signal-amplification techniques such as quantitative PCR enables the screening assay to be run using even trace amounts of target protein. Low picomolar amounts of proteins may therefore be accurately detected by quantitative PCR and $K_d$ measurements may be made in the picomolar range. The use of not only sensitive but also highly selective detection methods such as qPCR also eliminates the potential problem of non-specific protein interference and renders unnecessary protein purification steps and other types of manipulation normally done to protein samples that are analyzed using more traditional techniques. The present invention therefore provides for a fast, efficient and high-volume screening method requiring only small amounts of cellular materials and proteins, and for those reasons, is a cost effective screening alternative to cell based assays.

Also provided herein is a kit for screening candidate molecules or test compounds that competitively bind to the protein of interest in the presence of a competing reference ligand that is known to bind to the protein of interest. Such a kit may be comprised of a reference ligand (or "bait"), which is optionally immobilized onto a solid support or a container, such as a well in a multiwell plate; a detectable nucleic acid tag; and a protein of interest capable of being "tagged" by the nucleic acid tag. Where the nucleic acid tag is detectable by qPCR, the kit may additionally include a PCR primer capable of recognizing a PCR initiation sequence in the nucleic acid tag. Such a kit may be used to carry out the competitive binding screening assay as described above.

In another embodiment, the kit may be used for detecting the presence of a molecule (such as a protein of interest) that binds directly to the reference or "bait" ligand. In a more specific embodiment, such a kit may be a diagnostic kit for testing biological samples for the presence of a certain molecule, whether a chemical compound, peptide or protein. In one example, the kit comprises a bait molecule immobilized to a solid surface; a protein of interest capable of being tagged by the nucleic acid tag; and a detectable nucleic acid tag. The kit may optionally further comprise a PCR primer capable of recognizing a PCR initiation sequence in the nucleic acid tag to allow for qPCR amplification. In such a kit, the bait molecule is present at an optimized concentration so that the presence of a molecule, such as a peptide, protein, or a chemical compound, that binds to the bait molecule, can be detected by the reduction in signal due to the reduction of binding of the protein of interest which can also bind to the bait molecule. In one particular embodiment, the detectable protein is an antibody capable of being tagged by the nucleic acid tag. In a more specific embodiment, the detectable protein is an antibody fused to a DNA binding domain capable of forming a complex with a nucleic acid tag. Such a diagnostic kit may be used to test biological samples such as blood, saliva, urine, semen or other specimens, for the presence of antigen markers in order to determine or to confirm the presence of certain biological markers to determine, for example, a patient's diseased state. The diagnostic test may also be used to detect the presence of native or synthetic hormones or chemical compounds in a biological sample. In another embodiment, the diagnostic kit may be used to test environmental samples for the presence of a chemical or biological molecule, in certain cases derived from a pathogen, that binds to the reference or "bait" ligand.

The following examples are intended to serve as illustrations of the invention and are not to be taken as a limitation of the invention.

EXAMPLES

The practice of the system and methods provided herein employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields as are within the skill of the art. These techniques are described in the references cited herein and are fully explained in the literature. See, e.g., Maniatis et al. (1982) *Molecular Cloning: A Laboratory Manual*, Cold Spring Harbor Laboratory Press; Sambrook et al. (2001), *Molecular Cloning: A Laboratory Manual*, Third Edition, Cold Spring Harbor Laboratory Press; Ausubel et al., *Current Protocols in Molecular Biology*, John Wiley & Sons (1987 and annual updates through present); Gait (ed.) (1984) *Oligonucleotide Synthesis: A Practical Approach*, IRL Press; Eckstein (ed.) (1991) *Oligonucleotides and Analogues: A Practical Approach*, IRL Press; Birren et al. (eds.) *Genome Analysis: A Laboratory Manual* (1999) Cold Spring Harbor Laboratory Press.

Construction of Transient Mammalian In Vitro Expression Vector

The genetic elements listed below were cloned into the backbone of a generic bacterial plasmid pGEM by gene synthesis followed by restriction digest and subsequent ligation using standard molecular biology techniques. Listed from 5' end to 3' end, they are:

The CMV (Cytomegalovirus) enhancer/promoter region to allow strong, constitutive expression in many cell types, A chimeric intron composed of the first intron of the human β-globin gene and the intron that is between the leader and the body of an immunoglobulin gene heavy chain variable region (transfection studies have demonstrated that the presence of an intron flanking the cDNA insert frequently increases the level of gene expression), The DNA-binding domain of the yeast GAL4 or the human NF-κB transcriptional activators (see Table 1) fused in-frame with the TEV (Tobacco Etch Virus) protease recognition sequence followed by a multiple cloning region with several unique restriction sites, The SV40 (Simian Virus 40) late polyadenylation signal for enhanced mRNA stability and translation, The pMB 1 origin of replication for propagation in *E. coli*, and The Ampicillin resistance ($Amp^R$) gene for selection/propagation in *E. coli*.

Cloning of Kinases

The human p38α (GenBank No. NP_620581.1) and BRAF (GenBank No. NP_004324.1) kinase sequences were fused in-frame with the DNA-binding domain (GAL4 or NF-κB; See Table 1) were cloned by restriction digestion followed by ligation using standard molecular cloning protocols. The sequence of the clones was verified by ABI sequencing.

Transient In Vitro Expression and Protein Extract Preparation

Transient in vitro expression in human embryonic kidney (HEK) 293 cells was carried out using Lipofectamine® (Invitrogen) and sequence-verified plasmid DNA obtained using standard Qiagen plasmid purification kits. Transfections were performed for 24 hours at 37° C. using 80% confluent cells in 10 cm round Petri plates.

Protein extractions were carried out at 4° C. using extraction buffer M-PER (Pierce) containing 150 mM NaCl, 10 mM DTT and Complete™ (Roche) antiprotease mixture. Cells were lysed directly on the plate after a cold PBS wash and the cellular debris were removed by centrifugation. Protein concentrations were estimated by Bradford protein dosage assay (Bio-Rad). The extracts were aliquoted, frozen in liquid nitrogen and stored at −80° C. until use.

The level and quality of expression of every DNA construct were analyzed by SDS-PAGE/Western blotting using antibodies raised against GAL4 and NF-κB (Santa Cruz Biotechnology).

Construction of Nucleic Acid Tags

Random sequences were generated and used to design the amplicon sequence using the software Primer Express® (ABI). The amplicon sequence was BLAST searched against the human kinome, the T7 phage genome, and against other amplicon sequences and selected based on least similarity to the sequences in the BLAST search. The selected amplicon sequence was sent to ABI and the appropriate primer and qPCR fluorescent probe were prepared by ABI. The amplicon sequence was further modified by the addition of the GAL4 or NF-κB recognition sites, to create the complete nucleic acid tag. The oligonucleotide was cloned into bacterial plasmid, and the tag was replicated using PCR.

Competitive Binding Assay

The affinity resins for the competitive binding assays were prepared as follows. Dynabeads™ M280 (Streptavidin (Dynal #602.10)) were resuspended by shaking and swirling, and the beads were suspended at 10 mg/mL with 0.4 mg to be used per assay well. The beads were washed three times and resuspended in 1×PBS/0.05% Tween 20 (PBST) to 10 mg/mL and distributed in 2 mL tubes. Techniques for the preparation of biotinylated reference ligands are known, see, e.g., U.S. Publication No. 20050153371 The biotinylated reference moiety was added to the tubes at a molar ratio of 0.025-0.25:1 (reference ligand:biotin-binding capacity), mixed and incubated on the rotator for 30 minutes at room temperature. The beads were then blocked with excess biotin (molar ratio of 2:1 biotin to biotin-binding capacity) and washed with blocking buffer (SeaBlock (Pierce), 1% BSA, 0.05% Tween 20, 1 mM DTT) to remove unbound ligand and to reduce non-specific protein binding.

Polystyrene plates were blocked with 200 μL SBTB (Pierce #37527 SeaBlock/1% BSA, 0.05% Tween 20) per well. The bead solution from the previous step was added to the polystyrene plates at 12.5 uL of beads per well without removal of SBTB. The plates were shaken briefly at 700 rpm (wash 1), followed by pelleting, decanting, and another wash with shaking with SBTB (wash 2), followed by a third wash where the beads were shaken for at least 15 minutes in SBTB.

Test compounds were prepared as 1000× stocks in DMSO and rapidly diluted into the aqueous environment (1% DMSO final). DMSO (final concentration at 1%) was added to control assays lacking a test compound.

Protein extracts were slowly thawed in ice and diluted with 1× Binding Buffer (20% SeaBlock, 0.17×PBS, 0.05% Tween 20, 6 mM DTT). Binding reactions were assembled in the bead-containing polystyrene plates by combining the diluted protein extract and 1 μL of a test molecule in DMSO having a final concentration of 2 nM to 30 μM, in 1× Binding Buffer containing 10 nM of the nucleic acid tag (a chimeric DNA oligonucleotide encompassing the target sequence bound by GAL4 or NF-κB and a unit of amplification (Amplicon) for quantitative PCR detection). The assay plates were incubated at room temperature with shaking for 1 hour, and the affinity beads were washed four times with wash buffer (1×PBS, 0.05% Tween 20, 1 mM DTT) to remove unbound proteins. After the final wash, the beads were resuspended in Elution Buffer (1×PBS, 0.05% Tween 20, and 2 µM non-biotinylated affinity ligand) and incubated at room temperature with shaking for 30 minutes. The amount of kinase in the eluates was measured by quantitative PCR. Alternatively, the binding reaction may be carried out in the absence of the nucleic acid tag, which may be added later after the wash step to remove the unbound proteins.

Competitive Binding Assay with p38 MAP Kinase

The competitive binding assay features the p38 protein expressed in HEK293 cells and an immobilized ligand which binds the p38 ATP-binding site. To produce the p38 protein, the encoding region for p38α was fused in-frame with the DNA-binding domain of GAL4 or NF-κB and cloned into the expression vector as described above using standard cloning protocols. SB202190, a compound known to bind the p38 ATP-binding site with high affinity, was used as the immobilized reference ligand. A biotinylated flexible linker was attached to SB202190 at a position which would not interfere with the p38 binding site. SB202190 was then immobilized onto streptavidin-coated magnetic beads via its biotinylated linker.

Figure 2:
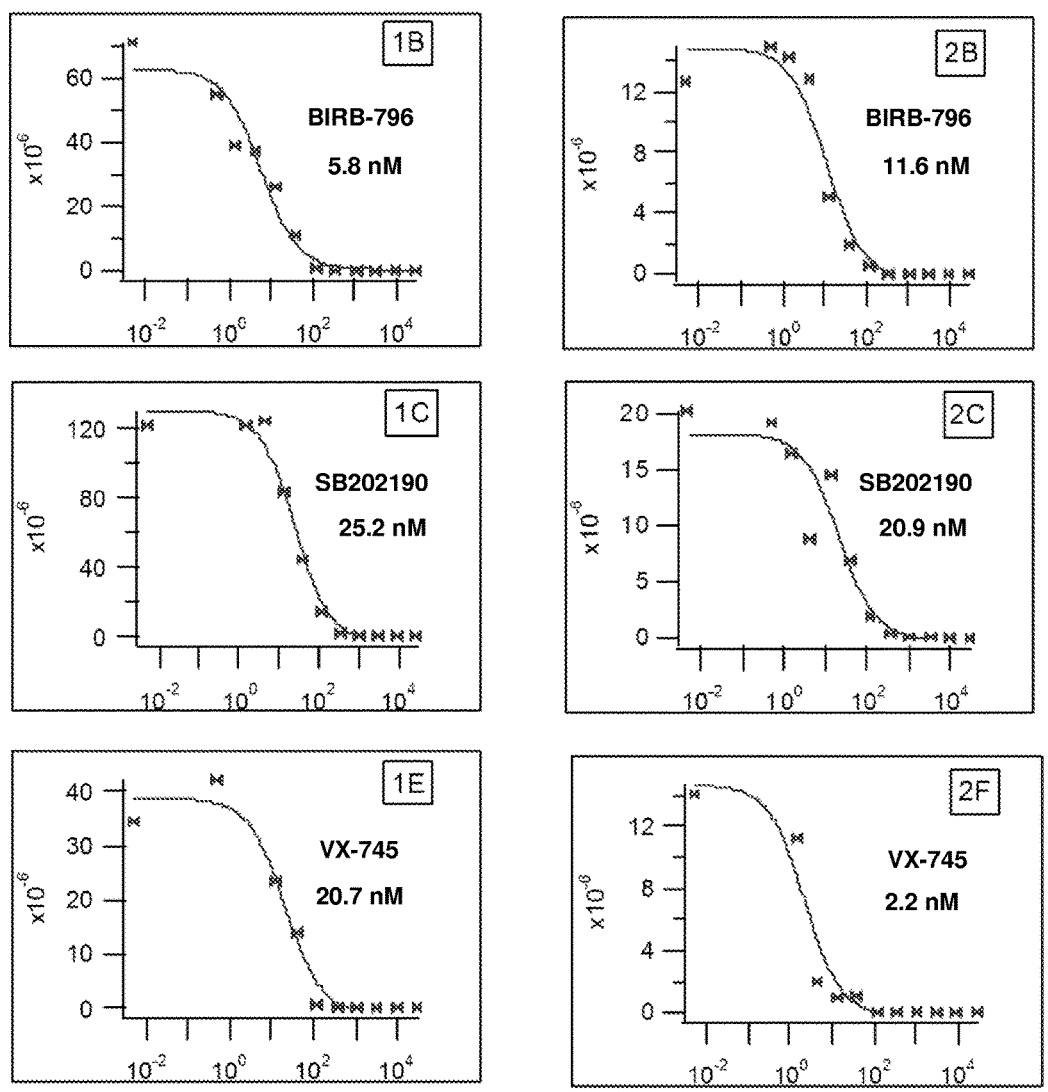
FIG. 2 provides a binding curve with calculated $K_d$s for p38 interaction with known kinase inhibitors BIRB-796, SB202190 and VX-745. SB202190 was used as immobilized reference ligand, and the nucleic acid tag used was a fusion comprising a GAL4 target DNA sequence and a PCR-amplifiable DNA sequence.
Figure 3:
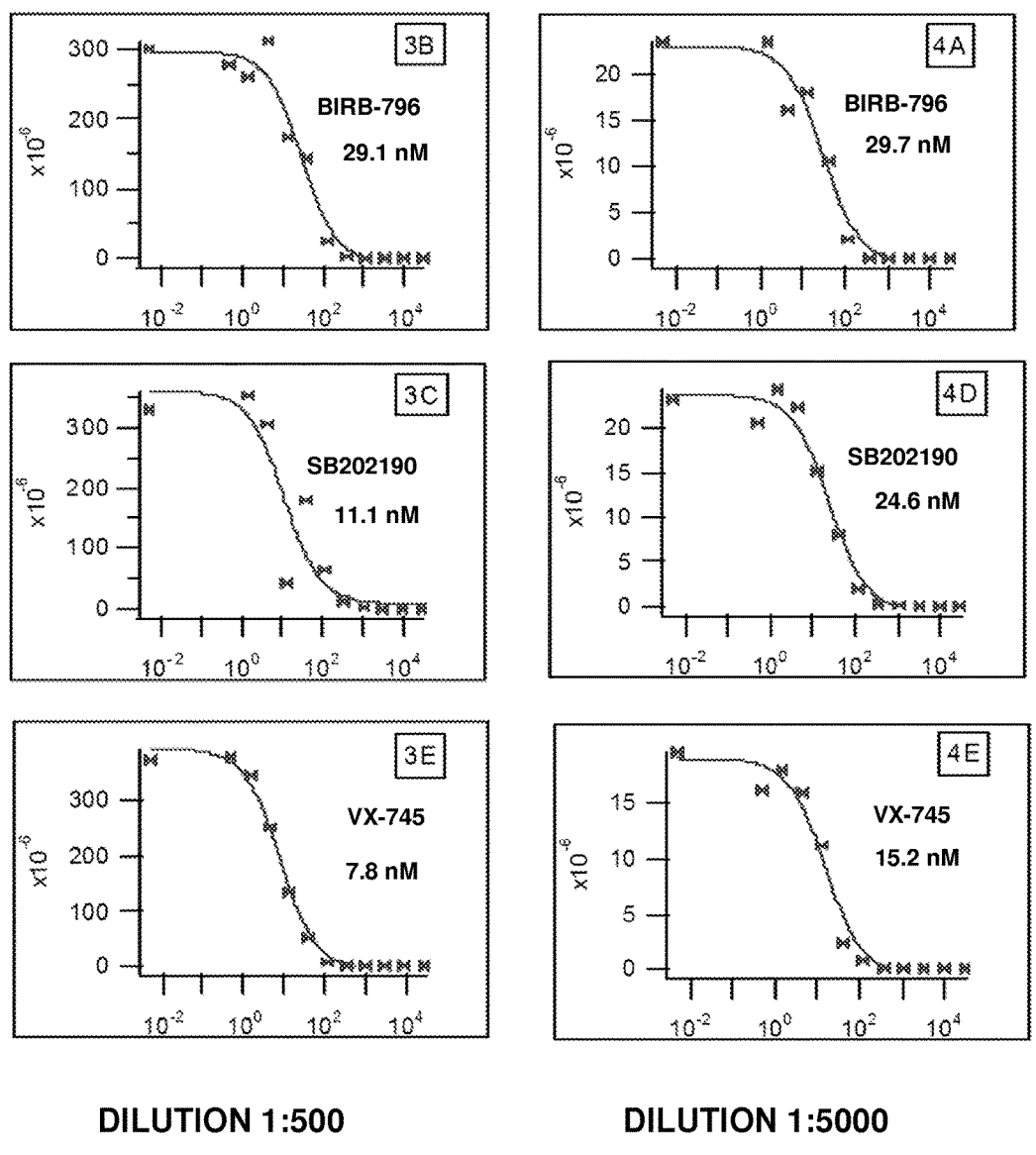
FIG. 3 provides a binding curve with calculated $K_d$s for p38 interaction with known kinase inhibitors BIRB-796, SB202190 and VX-745. SB202190 was used as immobilized bait, and the nucleic acid tag used was a fusion comprising a NF-κB target DNA sequence and a PCR-amplifiable DNA sequence.

Three compounds were tested for their ability to compete with the interaction between p38 and immobilized SB202190: SB201290 (unmodified and free in solution), BIRB-796 and VX-745. To determine the affinity of the interactions, the amount of p38 bound to the solid support was quantified as a function of concentration of test compound. $K_d$s for the three compounds are shown in FIGS. 2 and 3.

Competitive Binding Assay with BRAF Kinase

To produce the BRAF kinase protein, the encoding region for BRAF was fused in-frame with the DNA-binding domain of GAL4 or NF-κB (see Table 1), cloned into the expression vector described above and then expressed in HEK293 cells. PD-173955, a compound known to bind to the BRAF ATP-binding site with high affinity, was used as the immobilized reference ligand. This linked compound was produced using the same strategy used to create the SB202190 bait.

Figure 4:
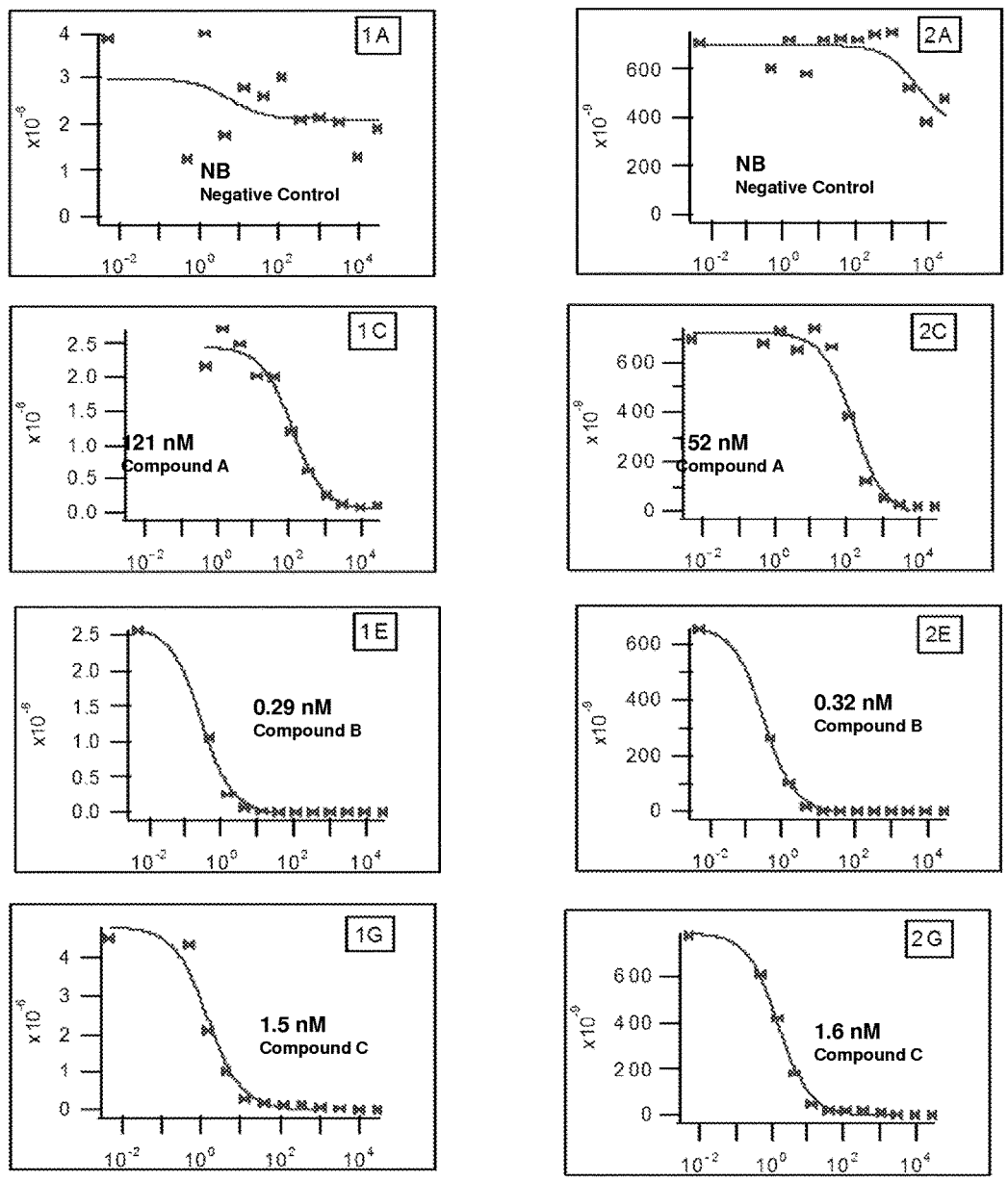
FIG. 4 provides a binding curve with calculated $K_d$s for BRAF interaction with four internal proprietary compounds. Three of the compounds, A, B and C are kinase inhibitors and one of the compounds which is not a kinase inhibitor, served as negative control. The interaction was detected using a nucleic acid tag comprising a GAL4 target DNA sequence and a PCR-amplifiable DNA sequence.
Figure 5:
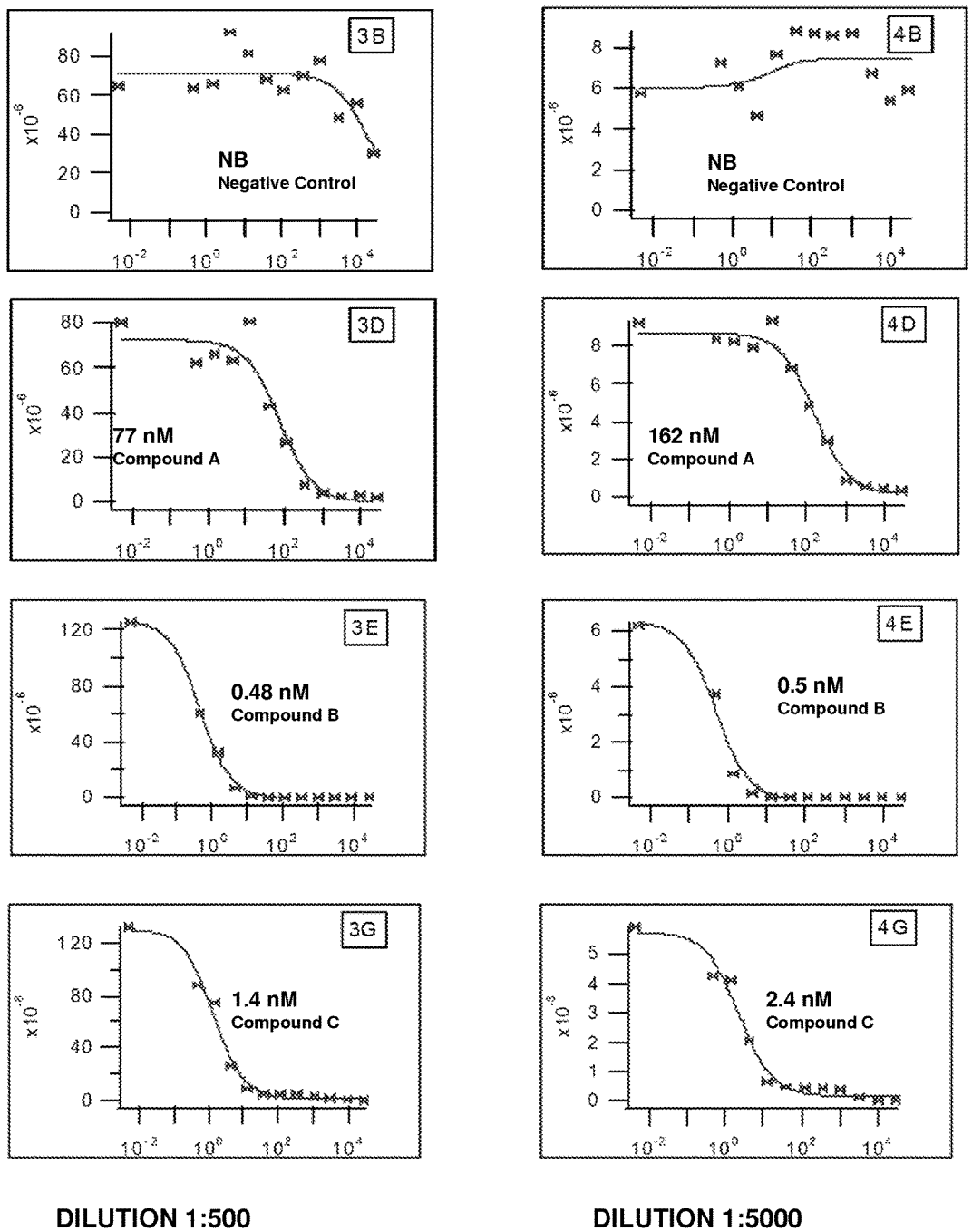
FIG. 5 provides a binding curve with calculated $K_d$s for BRAF interaction with four internal proprietary compounds. Three of the compounds, A, B and C are kinase inhibitors and one of the compounds which is not a kinase inhibitor, served as negative control. The interaction was detected using a nucleic acid tag comprising a NF-κB target DNA sequence and a PCR-amplifiable DNA sequence.

Four proprietary test compounds were tested for their ability to compete with the interaction between BRAF and immobilized reference ligand. One of the four compounds is chemically related to the other three but does not bind to the reference ligand, and was used as a negative control. To determine the affinity of the interactions, the amount of BRAF bound to the solid support was quantified as a function of concentration of test compound. $K_d$s for the four compounds are shown in FIGS. 4 and 5.

Competitive Binding Assay with a Panel of Kinases

Table 2 below shows signal-to-background ratios for competitive binding assays run for a panel of kinases, wherein each kinase was prepared as a fusion protein with an NFκB DNA binding domain. Each kinase was tested using its cognate bait (reference ligand), in the presence or absence of a cocktail of potential competitor test compounds in solution that comprises several known ATP-competitive kinase inhibitors, using the protocol described above. A signal-to-background ratio of 30:1 is considered acceptable and a ratio of 100:1 is preferred.

TABLE 2

| Kinase | Signal-to-Background ratio (x:1) |
|---|---|
| ARAF1 | 90 |
| BMPR1B | 535 |
| BMPR2 | 93470 |
| CDC2L1 | <10 |
| CDK7 | 117 |
| DDR2 | 69 |
| IRAK3 | 10933 |
| MAP2K2 | 5827 |
| MAP3K10 | 7162 |
| MAP3K9 | 187077 |
| MYLK | 36637 |
| SHARK | 53 |
| FLT3 | 1307 |
| ZAP70 | 2192 |
| AURAK | 4469 |
| CSHK2A1 | 291 |
| p38-gamma | 3361 |
| VEGFR2 | 139975 |
| ANKK1 (SgK288) | 50 |
| RPS6KA4 | 960 |
| SNARK | 370 |
| MAPKAPK5 | 1100 |
| MAP2K3 | 90 |
| MAP2K1 | 14,000 |
| MAP2K4 | 780 |
| GSK3B | 1300 |
| LATS2 | 290 |
| PIK3CA | 240 |
| PIK3CA (E545K) | 260 |
| PRKCE | 50 |
| MYLK | 270 |
| IKK-ε | 80 |

Multiplexed Competitive Binding Assay

The competitive binding assay was multiplexed in the following manner: The DNA-binding region of NF-κB was selected as the fusion partner for the kinases, based on the high affinity of the NF-κB DNA-binding domain for its cognate DNA and its long protein-DNA complex half life of 4-40 hours. The competitive binding assay involved preparing the liganded bead by adding the biotinylated reference ligand bait to the beads at the molar ratio range of 0.0025-0.25:1 and processed in the manner described above. The preparation of the protein extract involved a two-step dilution. At the first dilution step each protein extract stock was diluted 100-fold with 1×PBS/0.05% Tween 20/0.1% BSA/10 mM DTT at room temperature in the presence of 10 µM of a unique chimeric nucleic acid tag and 200 µg/mL salmon sperm DNA. The second dilution step was the multiplexing step where the different diluted extracts were combined and diluted another 100-fold in 1×PBS/0.05% Tween 20/0.1% BSA/10 mM DTT in the presence of 10 µM "qPCR-silent" decoy DNA, so that the final dilution yielded a 10,000-fold diluted stock containing 0.1-1 nM of each of the chimeric nucleic acid tag for each kinase fusion protein. In the situation where a particular kinase generating a strong assay signal was multiplexed with another kinase generating a weaker assay signal, the first dilution step for the strong-signaling kinase contained 100 nM, rather than 10 nM, of nucleic acid tag, in order to reduce the likelihood of the tag associated with the weak signaling kinase exchanging to a strong-signaling kinase at the step where the different kinase extracts were combined. The subsequent competitive binding assay step was run in the manner described above. At the readout step where the amount of binding is determined by qPCR, the eluate from the binding assay was aliquoted into different samples, and each sample read in a duplex format. Alternatively, the sample may be in a three-plex format using a three-color readout.

In one example, the beads were baited with staurosporine that was biotinylated through a PEG linker in the manner described in U.S. Publication No. 2005015337. Three kinases, PRKCE, ROCK2 and ZAP70, each fused in frame to the DNA-binding domain of NF-κB, were cloned and expressed in HEK293 cells. The protein extract of each kinase fusion was first diluted in buffer containing the 10 nM nucleic acid tag except for the sample containing the ZAP70 fusion protein, which was diluted in buffer containing 100 nM nucleic acid tag, since previous experiments had shown that ZAP70 fusion protein generated a stronger signal compared to the PRKCE and ROCK2 fusion proteins. The diluted extract was diluted further in the presence of "qPCR-silent" decoy DNA, and then combined with test compound and liganded beads for the competitive binding assay. The protein eluate obtained from the binding experiment was aliquoted into two samples, and each sample was assayed using two-color qPCR readout.

Competitive Binding Assay with Active and Inactive Kinase Conformations

The inactive form of the Ab11 kinase was prepared by lysing the HEK293 cells expressing the Ab11 fusion protein in 1× M-PER buffer (Pierce #78501) having 150 mM NaCl, 25× EDTA-free COMPLETE (Roche #11873 580 001) and 10 mM DTT. The protein extract was transferred to a PCR tube and incubated in a thermocycler at 30° C. for 45 minutes to allow the endogenous phosphatases in the cell extract to dephosphorylate the Ab11 protein, thereby increase the fraction of protein in the inactive (unphosphorylated) state.

The active form of the Ab11 kinase was prepared by first incubating for 2 hours immediately before the cell lysis/protein extraction step, the Ab11-transfected HEK293 cells in the following phosphatase inhibitors: either 2 mM sodium orthovandate (Calbiochem #567540) or 1× Phosphatase Inhibitor Cocktail Set II (Calbiochem #524625). The cells were lysed in 1× M-PER buffer (Pierce #78501) having 150 mM NaCl, 25× EDTA-free COMPLETE (Roche #11873 580 001), 10 mM DTT and 1× Phosphatase Inhibitor Cocktail Set II (Calbiochem #524625).

Figure 6A:
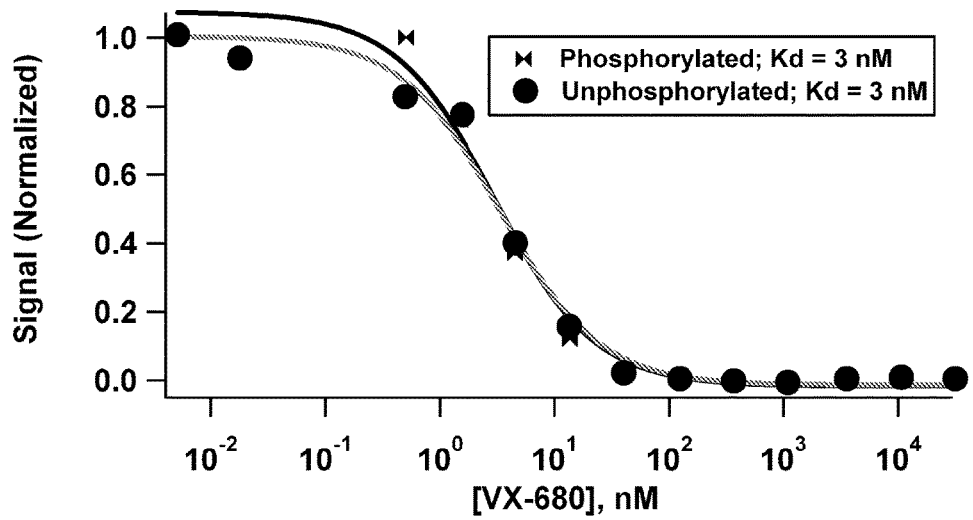
FIGS. 6A-6B show binding curves with calculated $K_d$s for interactions between the two forms of Ab1 (active and inactive) with (FIG. 6A) VX-680 or (FIG. 6B) imatinib. The interaction was detected using a nucleic acid tag comprising a NF-κB target DNA sequence and a PCR-amplifiable DNA sequence.
Figure 6B:
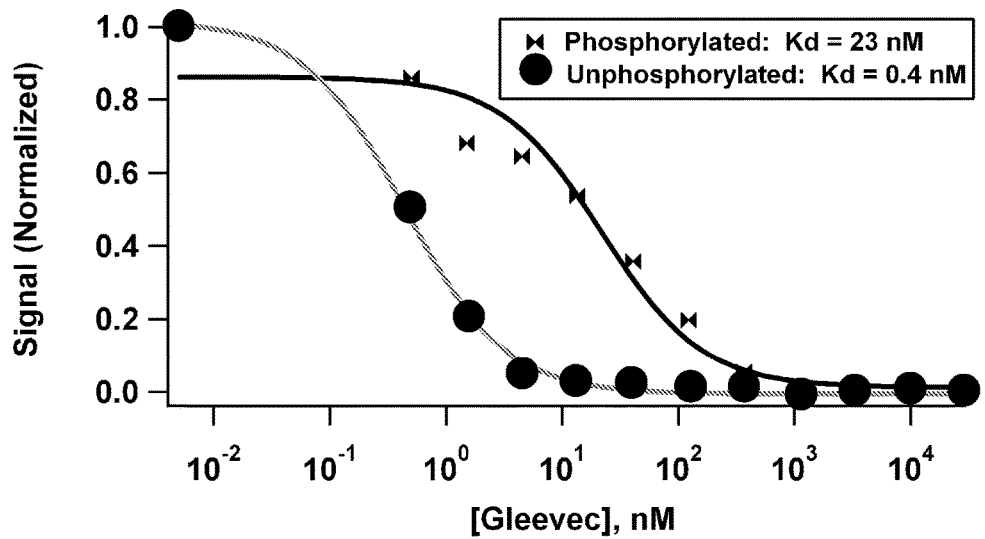

The active and inactive forms of Ab11 were used in a competitive binding assay performed in the manner described above, using Purvalanol B-bound beads as the immobilized bait. One of the compounds tested against both active and inactive forms of the kinase was VX-680, which is a compound known in the literature to be capable of binding to the active form of Ab1 (Young et al. (2006) Cancer Res 66(2): 1007-1014). The second compound that was chosen to be tested against the active/inactive kinase conformations was imatinib (STI571) which is a compound to be an inhibitor that preferentially binds to the inactive conformation of Ab11 (Schindler, T. et al. Science (2000) 289:1938-1942, Liu et al. Nature Chemical Biology (2006) 2(7):358-364). Kd values for both VX-680 and imatinib to the active phosphorylated and inactive unphosphorylated forms of Ab1 are shown in FIG. 6A. FIG. 6A shows that the Kd for VX-680 to Ab1 remains unchanged between the phosphorylated and unphosphorylated Ab1 kinase. This data provides confirmation for the first time that the compound is able to bind to Ab1 in the inactive conformation. By contrast, FIG. 6B shows that the Kd for imatinib is lower in the unphosphorylated form of Ab1 compared to the phosphorylated form, which indicates that the compound preferentially binds to the inactive form.

Competitive Binding Assay to Identify Non-ATP Competitive Kinase Inhibitors

The reference ligands used as bait in the competitive binding assays described herein are generally larger than the ATP molecule itself. These reference ligands therefore bind to more than the ATP-binding site, and they are more accurately described as binding the active site, which includes the canonical ATP-binding site and adjacent regions, such as the substrate binding site and the inter-domain cleft. These reference ligands therefore have the ability to displace not only binders of the ATP-binding site, but also binders that bind adjacent to the ATP site, including those that bind to the substrate binding site.

In one experiment designed to confirm the non-ATP competitive nature of the binding of BMS-345541 to IKKβ, a compound previously identified as binding to the active site of IKKβ, was biotinylated and used as a reference bait. BMS-345541 was previously shown by multiple inhibition analyses to bind to a site in a manner that was non-mutually exclusive with ADP/ATP, and which therefore was determined to be a non-ATP competitive binder (Burke et al. J of Biol Chem (2003) 278(3):1450-1456). The binding experiment with IKKβ kinase was carried out in the manner already described, but in addition, 20 mM of $MgCl_2$ and ATP at a concentration calculated to be ten times the $K_d$ of ATP for IKKβ was added to the reaction mixture in the assay measuring binding activity in the presence of ATP. A parallel experiment with IKKβ kinase was run using a known ATP-competitive molecule, staurosporine, as an ATP-competitive control. The results of the competitive binding experiment are shown in Table 3. The results show that while the ATP-competitive binder staurosporine displays an upward shift in Kd in the presence of ATP, BMS-345541 displays Kd values that are unaffected by ATP, which confirms that the molecule is a classic non-ATP competitive binder.

In a second experiment, designed to confirm the non-ATP competitive nature of the binding of PD184352 to MEK1 and MEK2, a compound identified as binding to the active site of MEK1 and MEK2 kinases, was used as the reference bait. PD184352 was previously shown by X-ray crystallography to bind to a novel binding pocket separate from but adjacent to the ATP-binding site, and was determined to be a non-ATP competitive binder (See, e.g., Ohren et al. Nature Structural & Molecular Biology (2004) 11(12):1192-1197). The MEK 1 kinase binding experiment was carried out in the manner described above, except that at the binding reaction step, 20 mM of $MgCl_2$ and ATP at a concentration calculated to be ten times the $K_d$ of ATP for MEK1, was added to the reaction mixture for the assay measuring binding activity in the presence of ATP. Similarly, the binding reaction for the MEK2 kinase binding assay contained, in addition to the standard binding assay mixture, 20 mM of $MgCl_2$ and ATP at a concentration calculated to be ten times the $K_d$ of ATP for MEK2. Staurosporine, a known ATP-competitive binder, was also tested in both MEK assays to provide an ATP-competitive control. The results of the competitive binding assay in the presence and absence of ATP are shown in Tables 4 and 5. The results show a marked decrease in the apparent $K_d$ of PD184352 to MEK1/2 in the presence of ATP, in contrast to the marked increase in apparent $K_d$ of staurosporine to MEK1/2 as would be expected for a compound which is ATP competitive. The fact that ATP has the effect of decreasing the apparent $K_d$ rather than having no effect on the apparent $K_d$ as was the case for BMS-345541, suggests that PD184352 binds preferentially to the ATP-bound MEK compared to unbound MEK, and is therefore an ATP-cooperative non-ATP competitive binder.

TABLE 3

IKKβ Competitive Binding Assay in the presence and absence of ATP

| Compound | Kd (nM) ATP not present | Kd (nM) ATP present |
|---|---|---|
| Staurosporine | 40 | 382 |
| BMS-345541 | 138 | 123 |

TABLE 4

MEK1 Competitive Binding Assay in the presence and absence of ATP

| Compound | Kd (nM) ATP not present | Kd (nM) ATP present |
|---|---|---|
| Staurosporine | 33 | 151 |
| PD184352 | 804 | 4 |

TABLE 5

MEK2 Competitive Binding Assay in the presence and absence of ATP

| Compound | Kd (nM) ATP not present | Kd (nM) ATP present |
|---|---|---|
| Staurosporine | 24 | 99 |
| PD184352 | 849 | 8 |

Cloning of hAGT Fusion Protein

A mammalian expression vector encoding a human $O^6$-alkylguanine DNA alkyltransferase (hAGT) was constructed using standard molecular cloning procedures. The genetic elements in the cloning vector comprised, from 5' end to 3' end, a CMV enhancer/promoter, the sequence encoding the human $O^6$-alkylguanine DNA alkyltransferase fused in frame with the TEV protease recognition sequence, followed by a full-length p38α kinase followed by a sequence encoding the HA11 epitope tag.

The hAGT fusion protein was expressed in HEK293 cells in vitro.

A nucleic acid tag can be constructed by linking the $O^6$-benzylguanine-polyethylene glycol maleimide (Covalys) to a DNA sequence comprising the PCR amplification marker. The nucleic acid tagged substrate may be recognized by the hAGT fusion protein which will transfer the nucleic acid label to be covalently bound to the fusion protein.

All publications and patent applications mentioned in this specification are herein incorporated by reference to the same extent as if each individual publication or patent application was specifically and individually indicated to be incorporated by reference

What is claimed is:

1. A method for detecting a protein of interest that binds to a ligand, comprising:
   (a) contacting the ligand, which is immobilized on a solid support container, with a fusion protein,
   (b) said fusion protein comprising (i) a first protein domain comprising the protein of interest that binds to the ligand, and (ii) a second protein domain comprising a nucleic acid-interacting motif, wherein the protein of interest and the nucleic acid-interacting motif differ from each other;
   (c) adding to said container a nucleic acid oligomer comprising (i) a first nucleic acid sequence that is a PCR amplification sequence not having a recognition sequence for said nucleic acid-interacting motif of said fusion protein, and (ii) a second nucleic acid sequence that binds the nucleic acid-interacting motif of said fusion protein, wherein the first nucleic acid sequence is heterologous to the second nucleic acid sequence;
   (d) allowing binding in the container among the fusion protein, the ligand, and the nucleic acid oligomer;
   (e) removing unbound nucleic acid oligomer and unbound fusion protein; and
   (f) detecting whether the nucleic acid oligomer is bound to the ligand, whereby detection of bound nucleic acid oligomer indicates that the protein of interest binds to the ligand.

2. The method of claim 1, wherein the nucleic acid-interacting motif of the fusion protein is an NFκB amino acid sequence or a GAL4 amino acid sequence.

3. The method of claim 1, further comprising a step of identifying a test compound that binds to the protein of interest, wherein the ligand is a reference ligand known to bind to the protein of interest, comprising:
   carrying out said step (a) of contacting the ligand with the fusion protein in the presence of the test compound, wherein a reduction in the amount of fusion protein bound to the reference ligand in the presence of test compound as compared to the absence of test compound indicates that the test compound competes for binding of the protein of interest to the reference ligand.

4. The method of claim 3, wherein the protein of interest has an ATP-binding site, and said step (a) of contacting the ligand with the fusion protein is done (i) in the presence and absence of test compound, and (ii) in the presence and absence of exogenous ATP, wherein a reduction in the amount of fusion protein bound to the immobilized reference ligand in the presence of test compound and absence of ATP, as compared to the absence of test compound and absence of ATP, indicates the test compound binds the protein of interest.

5. The method of claim 1, further comprising qPCR amplifying the nucleic acid oligomer that is bound to the fusion protein.

6. The method of claim 3, wherein the nucleic acid oligomer is radiolabeled, fluorescently labeled or biotinylated.

7. The method of claim 3, wherein the protein of interest is either a transmembrane protein, transmembrane ion channel protein, ligand gated ion channel protein, nuclear hormone receptor protein, extracellular signaling molecule or factor, cytokine, growth factor, hormone, enzyme, antibody small chain variable fragment (scFv) or a protein kinase.

8. The method of claim 3, wherein the nucleic acid-interacting motif of the fusion protein is an NFκB amino acid sequence or a GAL4 amino acid sequence.

9. The method of claim 3, further comprising a step of detecting whether the nucleic acid oligomer is bound to the ligand using varying concentrations of test compound and further comprising a step of using calculating an equilibrium dissociation constant ($K_d$) for the interaction between the protein of interest and the test compound.

10. The method of claim 1, wherein the protein of interest is a human protein kinase.

11. The method of claim 10, wherein the reference ligand is SB202190, staurosporine, purvalanol B, SU5402, imatinib mesylate, SU6668, Iressa or PD-173955.

12. The method of claim 10, wherein the kinase is a non-receptor tyrosine kinase.

13. The method of claim 12, wherein the non-receptor tyrosine kinase is a member of the ABL, ACK, CSK, MATK, FAK, PYK2, FES, FRK, JAK, SRC-A, SRC-B, TEC, or SYK family of tyrosine kinases.

14. The method of claim 10, wherein the kinase is a receptor tyrosine kinase.

15. The method of claim 14, wherein the receptor tyrosine kinase is a member of the ALK, AXL, DDR, EGFR, EPH, FGFR, INSR, MET, MUSK, PDGFR, PTK7, RET, ROR, ROS, RYK, TIE, TRK, VEGFR, AATYK, or SuRTK106 family of tyrosine kinases.

16. The method of claim 10, wherein the kinase is a serine-threonine kinase.

17. A method of determining the $K_d$ value of a test compound for a protein of interest, comprising:
   (a) contacting in the presence of varying concentrations of and absence of test compound, an immobilized reference ligand, which binds the protein of interest, with a chimeric fusion protein, said chimeric fusion protein comprising (i) a first protein domain comprising the protein of interest, and (ii) a second, different protein domain comprising a nucleic acid-interacting motif, wherein the protein of interest and the nucleic acid interacting motif differ from each other;
   (b) adding to said chimeric fusion protein a nucleic acid oligomer comprising (i) a first nucleic acid sequence that is a PCR amplification sequence not having a recognition sequence for said nucleic acid-interacting motif of said fusion protein, and (ii) a second nucleic acid sequence that binds the nucleic acid-interacting motif of said fusion protein, wherein the first nucleic acid sequence is heterologous to the second nucleic acid sequence;
   (c) removing unbound nucleic acid oligomer and unbound fusion protein; and
   (d) obtaining a competitive binding curve by detecting or otherwise quantitating the nucleic acid oligomer that is bound to the fusion protein retained on the solid support at each of the varying concentrations of and absence of test compound;
   whereby the $K_d$ value of the test compound for the protein of interest is the concentration at which the protein of interest retained by the immobilized reference ligand in the presence of test compound is 50% of the protein of interest retained in the absence of test compound.

18. A method of simultaneously identifying a test compound that binds to two or more proteins of interest, comprising:
   (a) contacting, in the presence and absence of test compound, an immobilized reference ligand, which binds each of the two or more proteins of interest, with two or more chimeric fusion proteins, wherein each fusion protein independently comprises (i) a first protein domain comprising only one of the two or more proteins of interest, and (ii) a different second protein domain comprising a nucleic acid-interacting motif, wherein the protein of interest and the nucleic acid-interacting motif differ from each other;
   (b) adding two or more nucleic acid oligomers, wherein each of the two or more nucleic acid oligomers comprises a first nucleic acid sequence that independently binds the nucleic acid-interacting motif of only one of the two or more fusion proteins and a second, heterologous, nucleic acid sequence that is a PCR amplification sequence not having a recognition sequence for said nucleic acid-interacting motif of said fusion proteins;
   (c) removing unbound nucleic acid oligomer and unbound fusion protein; and
   (d) detecting or otherwise quantitating each of the two or more nucleic acid oligomers;
   wherein a reduction in the amount of each of the two or more fusion proteins bound to the immobilized reference ligand in the presence of test compound as compared to the absence of test compound indicates the test compound binds the respective two or more proteins of interest.

19. The method of claim 18, wherein the nucleic acid oligomers are radiolabeled, fluorescently labeled or biotinylated.

20. The method of claim 18, wherein the reference ligand is immobilized on a multiwell plate.

21. The method of claim 18, wherein the proteins of interest are protein kinases.

22. The method of claim 18, further comprising determining in a well the $K_d$ value of a test compound for two or more proteins of interest, comprising:
   (a) in the presence of varying concentrations of and absence of test compound, contacting in a well an immobilized reference ligand, which binds each of the two or more proteins of interest, with two or more chimeric fusion proteins, wherein each fusion protein independently comprises (i) a first protein domain comprising only one of the two or more proteins of interest, and (ii) a second, different protein domain comprising a nucleic acid-interacting motif, wherein the protein of interest and the nucleic acid-interacting motif differ from each other;
   (b) adding two or more nucleic acid oligomers, wherein each of the two or more nucleic acid oligomers comprises a first nucleic acid sequence that independently binds the nucleic acid interacting motif of only one of the two or more fusion proteins and a second, heterologous, nucleic acid sequence that is a PCR amplification sequence;
   (c) removing unbound nucleic acid oligomer and unbound fusion protein; and
   (d) obtaining a competitive binding curve by detecting or otherwise quantitating each of the two or more nucleic acid oligomers that is bound to the two or more fusion proteins retained on the solid support at each of the varying concentrations of and in the absence of test compound;
   whereby the $K_d$ value of the test compound for each of the two or more proteins of interest is the concentration at which each of the two or more proteins of interest retained by the immobilized reference ligand in the presence of test compound is 50% of the respective two or more proteins of interest retained in the absence of test compound.

23. The method of claim 1, wherein the protein of interest is a human protein.

* * * * *